(12) United States Patent
Valdes et al.

(10) Patent No.: US 9,336,353 B2
(45) Date of Patent: May 10, 2016

(54) SYSTEMS AND METHODS FOR COMMUNICATING SENSOR DATA BETWEEN COMMUNICATION DEVICES OF A GLUCOSE MONITORING SYSTEM

(75) Inventors: Jorge Valdes, San Diego, CA (US); Shawn Larvenz, Ramona, CA (US); Michael Robert Mensinger, San Diego, CA (US); Hari Hampapuram, San Diego, CA (US); Kostyantyn Snisarenko, San Diego, CA (US); Phil Mayou, San Diego, CA (US); Eli Reihman, San Diego, CA (US); Randy Tompot, Escondido, CA (US)

(73) Assignee: DexCom, Inc., San Diego, CA (US)

( * ) Notice: Subject to any disclaimer, the term of this patent is extended or adjusted under 35 U.S.C. 154(b) by 1310 days.

(21) Appl. No.: 13/167,602

(22) Filed: Jun. 23, 2011

(65) Prior Publication Data
US 2011/0320130 A1    Dec. 29, 2011

Related U.S. Application Data

(60) Provisional application No. 61/358,828, filed on Jun. 25, 2010.

(51) Int. Cl.
*G06F 19/00* (2011.01)

(52) U.S. Cl.
CPC ........ *G06F 19/3412* (2013.01); *G06F 19/3418* (2013.01)

(58) Field of Classification Search
CPC .. A61B 5/0002; A61B 5/1495; A61B 5/7275; A61B 5/743; A61B 5/0404; A61B 2560/0431; A61B 2560/0456; A61B 2560/0271; A61B 5/7445; A61B 5/14532; A61B 5/0022; G06F 19/3418; G06F 19/3406; G06F 19/363; G06F 19/3412; A61M 5/1723; A61M 2230/201; A96F 19/3406; H04L 67/125
USPC ........ 702/19, 104, 188; 600/365, 347; 435/14
See application file for complete search history.

(56) References Cited

U.S. PATENT DOCUMENTS 5,375,604 A * 12/1994 Kelly et al. ................... 600/484
5,507,288 A    4/1996 Bocker et al.
(Continued)

FOREIGN PATENT DOCUMENTS

WO    WO 96/37246    11/1996
WO    WO 97/01986    1/1997

OTHER PUBLICATIONS

What is background?—A Word Definition From the Webopedia Computer Dictionary, http://www.webopedia.com/TERM/B/background.html, Copyright 2014 QuinStreet Inc., Downloaded Aug. 8, 2014.

*Primary Examiner* — Carol S Tsai
(74) *Attorney, Agent, or Firm* — Knobbe Martens Olson & Bear, LLP

(57) ABSTRACT

System and method for communicating glucose concentration information between devices of a continuous glucose monitoring system is provided. The continuous glucose monitoring system can include a sensor module generates a glucose concentration measurement data and transmits the data to one or more further devices of the continuous glucose monitoring system. The further devices can include a receiver unit and one or more secondary display devices. The receiver unit can be configured to be a stand-alone device of or physically connect to a secondary display device. A user interface can also be provided that provides enhanced functionality for using the continuous glucose monitoring system.

11 Claims, 10 Drawing Sheets

(56) References Cited

U.S. PATENT DOCUMENTS

| | | | |
|---|---|---|---|
| 5,665,065 A | 9/1997 | Colman et al. | |
| 5,772,586 A | 6/1998 | Heinonen et al. | |
| 5,899,855 A | 5/1999 | Brown | |
| 5,995,860 A | 11/1999 | Sun et al. | |
| 6,396,416 B1 | 5/2002 | Kuusela et al. | |
| 6,428,475 B1 | 8/2002 | Shen | |
| 6,494,830 B1 | 12/2002 | Wessel | |
| 6,558,320 B1 | 5/2003 | Causey et al. | |
| 6,571,128 B2 | 5/2003 | Lebel et al. | |
| 6,641,533 B2 | 11/2003 | Causey et al. | |
| 6,699,188 B2 | 3/2004 | Wessel | |
| 6,958,705 B2 | 10/2005 | Lebel et al. | |
| 7,299,082 B2 | 11/2007 | Feldman et al. | |
| 7,447,596 B2 | 11/2008 | Kawatahara et al. | |
| 7,519,408 B2 | 4/2009 | Rasdal et al. | |
| 7,587,287 B2 | 9/2009 | Connolly et al. | |
| 7,591,801 B2 | 9/2009 | Brauker et al. | |
| 7,595,723 B2 | 9/2009 | Heitzmann et al. | |
| 7,602,310 B2 | 10/2009 | Mann et al. | |
| 7,722,536 B2 | 5/2010 | Goodnow | |
| 7,927,274 B2 | 4/2011 | Rasdal et al. | |
| 7,976,492 B2 | 7/2011 | Brauker et al. | |
| 8,029,459 B2 | 10/2011 | Rush et al. | |
| 8,029,460 B2 | 10/2011 | Rush et al. | |
| 8,260,393 B2 | 9/2012 | Kamath et al. | |
| 8,372,351 B2 * | 2/2013 | Ow-Wing | 422/403 |
| 2002/0044059 A1 * | 4/2002 | Reeder et al. | 340/573.1 |
| 2002/0161291 A1 * | 10/2002 | Kianl et al. | 600/324 |
| 2003/0050537 A1 | 3/2003 | Wessel | |
| 2003/0208113 A1 | 11/2003 | Mault et al. | |
| 2004/0210458 A1 * | 10/2004 | Evans et al. | 705/2 |
| 2005/0277164 A1 * | 12/2005 | Drucker et al. | 435/14 |
| 2006/0009684 A1 * | 1/2006 | Kim | 600/300 |
| 2007/0208245 A1 * | 9/2007 | Brauker et al. | 600/365 |
| 2007/0244383 A1 | 10/2007 | Talbot et al. | |
| 2007/0255115 A1 * | 11/2007 | Anglin et al. | 600/300 |
| 2008/0103377 A1 * | 5/2008 | Brown | 600/347 |
| 2008/0132974 A1 * | 6/2008 | Strother et al. | 607/60 |
| 2008/0221930 A1 * | 9/2008 | Wekell et al. | 705/3 |
| 2008/0228055 A1 * | 9/2008 | Sher | 600/365 |
| 2008/0300572 A1 * | 12/2008 | Rankers et al. | 604/504 |
| 2009/0005651 A1 * | 1/2009 | Ward et al. | 600/300 |
| 2009/0043525 A1 * | 2/2009 | Brauker et al. | 702/104 |
| 2009/0099864 A1 * | 4/2009 | Cronrath et al. | 705/2 |
| 2009/0105636 A1 * | 4/2009 | Hayter et al. | 604/66 |
| 2009/0131861 A1 * | 5/2009 | Braig et al. | 604/66 |
| 2009/0240193 A1 * | 9/2009 | Mensinger et al. | 604/66 |
| 2010/0095229 A1 | 4/2010 | Dixon et al. | |
| 2010/0137698 A1 | 6/2010 | Andrews et al. | |
| 2010/0299597 A1 * | 11/2010 | Shin et al. | 715/702 |
| 2010/0305421 A1 * | 12/2010 | Ow-Wing | 600/365 |
| 2010/0331650 A1 * | 12/2010 | Batman et al. | 600/365 |
| 2011/0118561 A1 * | 5/2011 | Tari et al. | 600/301 |

\* cited by examiner

SYSTEMS AND METHODS FOR COMMUNICATING SENSOR DATA BETWEEN COMMUNICATION DEVICES OF A GLUCOSE MONITORING SYSTEM

CROSS REFERENCE TO RELATED APPLICATIONS

This application claims the benefit of U.S. Provisional application No. 61/358,828, filed Jun. 25, 2010, the disclosure of which is incorporated by reference herein in its entirety, and is hereby made a part of this specification

FIELD OF THE INVENTION

System and method for communicating glucose concentration information between devices of a continuous glucose monitoring system is provided. The continuous glucose monitoring system can include a sensor module that generates glucose concentration measurement data and transmits the data to one or more further devices of the continuous glucose monitoring system. The further devices can include a receiver unit and one or more secondary display devices. The receiver unit can be configured to be a stand-alone device of or physically connect to a secondary display device. A user interface can also be provided that provides enhanced functionality for using the continuous glucose monitoring system.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically requires uncomfortable finger pricking methods. Due to the lack of comfort and convenience, a diabetic will normally only measure his or her glucose level two to four times per day. Unfortunately, these time intervals are spread so far apart that the diabetic will likely find out too late, sometimes incurring dangerous side effects, of a hyperglycemic or hypoglycemic condition. In fact, it is not only unlikely that a diabetic will take a timely SMBG value, but additionally the diabetic will not know if his blood glucose value is going up (higher) or down (lower) based on conventional methods.

Consequently, a variety of non-invasive, transdermal (e.g., transcutaneous) and/or implantable electrochemical sensors are being developed for continuously detecting and/or quantifying blood glucose values. These devices generally transmit raw or minimally processed data for subsequent analysis at a remote device, which can include a display.

SUMMARY OF THE INVENTION

Various implementations of systems, methods, and devices within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

In a first aspect, a glucose monitoring system is provided comprising a receiver unit configured to receive sensor data indicative of a glucose concentration in a host measured by a substantially continuous glucose sensor, the receiver unit comprising: (i) a user interface configured to interact with a user; (ii) a computer memory; (iii) a wireless receiver configured to receive sensor data transmitted from a substantially continuous glucose sensor electronics module, the electronics module operatively coupled to the substantially continuous glucose sensor; (iv) a battery configured to provide power to the receiver unit;(v) a housing enclosing the computer memory, the wireless receiver and the battery, wherein the user interface is at least partially disposed on the housing; (vi) a first communication port in the housing configured to permit mechanical removable attachment of the housing to a secondary display device, the first communication port also configured to provide electrical communication between the receiver unit and the secondary display device; (vii) a first processor coupled to the user interface, the computer memory, the wireless receiver, the first communication port and the battery; and (viii) a software program stored in the computer memory, the software program comprising instructions configured to perform: receiving sensor data from the substantially continuous glucose sensor, processing the received sensor data, the processing comprising generating displayable sensor data, displaying an indication of the displayable sensor data on the display, and transmitting the displayable sensor data to a secondary device via the first communication port.

In an embodiment of the first aspect, the glucose monitoring system further comprises a substantially continuous glucose sensor configured to measure in vivo glucose concentrations and to generate a signal indicative of the measured in vivo glucose concentrations; and substantially continuous glucose sensor electronics in electrical communication with the substantially continuous glucose sensor, the substantially continuous glucose sensor electronics comprising a second processor configured to generate the sensor data based on the signal generated by the substantially continuous glucose sensor and a wireless transmitter configured to transmit the sensor data to the wireless receiver of the receiver unit.

In an embodiment of the first aspect, the glucose monitoring system further comprises a reference glucose meter configured to measure a glucose concentration of an ex vivo sample of a host, wherein the glucose meter is operatively coupled to the first processor, and wherein the software program further comprises instructions for calibrating the sensor data using data generated by the reference glucose meter.

In an embodiment of the first aspect, the reference glucose meter is integral with the receiver unit.

In an embodiment of the first aspect, the glucose monitoring system further comprises the secondary display device, wherein the secondary display device is a handheld display device coupled to the first communication port and comprises software stored in a memory of the handheld display device, the software comprising instructions to display displayable data transmitted from the receiver unit via the first communication port on a display of the handheld display device.

In an embodiment of the first aspect, the housing of the receiver unit is configured to receive at least a portion of the handheld display device so as to physically couple the receiver unit to the handheld display device.

In an embodiment of the first aspect, the hand-held display device is a mobile telephone.

In an embodiment of the first aspect, the receiver unit is shaped to define a recess configured to accept an end of the handheld device.

In an embodiment of the first aspect, the software stored in the memory of the handheld device comprises a software application downloaded from a remote server via the internet.

In an embodiment of the first aspect, the software further comprises instructions for determining an occurrence of a predetermined event based on the processed received sensor data, and for initiating an alert upon the occurrence of the predetermined event, the alert comprising one or more of an audible alert, a vibratory alert or a visual alert, each of the alerts being performed using a communication unit user interface, wherein the predetermined event comprises an event selected from the group consisting of exceeding a hypoglycemia threshold, exceeding a hyperglycemia threshold, exceeding an approaching hypoglycemia threshold, exceeding an approaching hyperglycemia threshold, and exceeding a glucose concentration rate-of-change threshold.

In an embodiment of the first aspect, the user interface comprises one or more of a display configured to perform the visual alert, a vibrator motor configured to perform the vibratory alert, or an audio transducer configured to perform the audible alert.

In an embodiment of the first aspect, the receiver unit further comprises a wireless transreceiver configured to transmit data to a wireless receiver of a glucose sensor unit, wherein the receiver is incorporated in the transreceiver.

In an embodiment of the first aspect, the glucose monitoring system further comprises an insulin pump in signal communication with the receiver unit.

In an embodiment of the first aspect, the receiver unit further comprises a second communication port configured to provide for a wired universal serial bus connection to a computer device selected from the group consisting of a personal computer, a mobile telephone and a medical device controller.

In an embodiment of the first aspect, the first interface is configured to connect to a 30 pin connector of a mobile telephone.

In an embodiment of the first aspect, the housing is configured to enclose a plurality of sides of a mobile telephone.

In an embodiment of the first aspect, charging the battery further comprises charging a battery of a hand-held computer when the hand-held computer is connected to the first communication port.

In an embodiment of the first aspect, the sensor electronics are housed in a sensor electronics housing having a first adhesive patch affixed to an underside thereof and wherein the substantially continuous glucose sensor is at least partially housed in a sensor housing having a second adhesive patch affixed to an underside thereof, wherein sensor electronics housing is separate from the sensor housing and wherein the substantially continuous glucose sensor is in electrical communication with the sensor electronics via a cable attached at one end to the sensor housing and at the other end to the sensor electronics housing.

In a second aspect, a method is provided for processing, transmitting and displaying substantially continuous glucose sensor data, comprising: wirelessly receiving glucose sensor data in a first data format using a first computing device; processing the glucose sensor data to generate first displayable sensor data using the first computing device; displaying an indication of the first displayable sensor data on a display of the first computing device; electronically coupling the first computing device to a second computing device, the second computing device having a display that is larger than the display of the first computing device; converting at least some of the sensor data in the first data format into a second data format; transmitting the converted sensor data in the second data format to the second computing device; processing, using the second computing device, the converted sensor data to generate second displayable sensor data; and displaying an indication of the second displayable sensor data on the display of the second computing device.

In an embodiment of the second aspect, the second computing device is a mobile telephone.

In an embodiment of the second aspect, the method further comprises calibrating the sensor data using reference data obtained from a reference glucose meter.

In an embodiment of the second aspect, the reference glucose meter is integral with the first computing device.

In an embodiment of the second aspect, the coupling comprises coupling a communication port of the first computing device to a communication port of the second communication device.

In an embodiment of the second aspect, the first computing device comprises a housing comprising an opening shaped to enclose a portion of the second computing device, wherein the coupling comprises inserting at least a portion of the first computing device in the opening of the first computing device.

In a third aspect, a method is provided for configuring alert settings of a glucose monitoring system, comprising: providing a receiver module having a set of configurable alert settings, wherein each of the set of configurable alert settings is initially set to a first, default configuration; coupling the receiver unit to a secondary display device having a user interface configured to receive user input; receiving user input from the secondary display device indicative of one or more alert setting modifications; and modifying the one or more configurable alert settings in accordance with the user input into a second configuration that is different than the first, default configuration.

In an embodiment of the third aspect, the set of configurable alert settings comprises one or more settings selected from the group consisting of: a hypoglycemic setting, a hyperglycemic setting, a rate-of-change setting, and a calibration setting.

In an embodiment of the third aspect, the default settings comprise a setting indicative of a hypoglycemic event threshold and a setting indicative of a hyperglycemic event threshold, the method further comprising activating an alarm of the receiving module if one of the event thresholds is exceeded.

In an embodiment of the third aspect, the method further comprises automatically resetting the set of configurable alert settings to the default configuration upon the detection of a predetermined event.

In an embodiment of the third aspect, the predetermined event comprises one of a data corruption error, a low power indication, or a device hacking indication.

In a fourth aspect, a method is provided for validating a reference data value, comprising: (a) receiving a reference value inputted into a first computing device using a user interface of the first computing device; (b) storing the inputted reference data value in memory of the first computing device; (c) transmitting, using the first computing device, a first data packet indicating the reference data value; (d) receiving, using a second computing device, the first data packet; (e) processing, using the second computing device, the first data packet to determine the reference data value; (f) transmitting, using the second computing device, a second data packet indicating the reference data value; (g) receiving, using the first computing device, the second data packet; (h) processing, using the first computing device, the second data packet to determine the reference data value; (i) validating the reference data value, wherein validating comprises determining whether the reference data value determined from processing the second data packet matches the reference data value stored in memory of the first computing device; and (j) calibrating sensor data using the reference data value if the reference data value is valid.

In an embodiment of fourth aspect, the method further comprises displaying the reference data value determined during step (e) on a display of the second communication device.

In an embodiment of fourth aspect, step (i) further comprises comparing, using the first computing device, the data value determined from processing the second data packet with the reference data value stored in memory of the first computing device and wherein the reference data value is validated if the compared data values match.

In an embodiment of fourth aspect, step (i) further comprises displaying the data value determined from processing the second data packet on a display of the first computing device, prompting a user using the user interface for confirmation that the data value displayed on the display of the first computing device is valid, and receiving input responsive to the prompting.

In an embodiment of fourth aspect, the received input responsive to the prompting comprises an indication that the reference data value is valid.

In an embodiment of fourth aspect, the received input responsive to the prompting comprises an indication that the reference data value is invalid.

In an embodiment of fourth aspect, the method further comprises transmitting, using the first computing device, a third data packet to a third computing device indicative of the reference value being valid, wherein the third computing device performs step (j).

In an embodiment of fourth aspect, the first computing device is a mobile telephone, the second computing device is a receiver unit and the third device is a sensor electronics module.

In an embodiment of fourth aspect, a housing of the first computing device is releasably coupled to a housing of the second computing device.

In an embodiment of fourth aspect, steps (c), (d), (f), and (g) are performed via a wired communication interface that electronically couples the first computing device with the second computing device.

In an embodiment of fourth aspect, steps (c), (d), (f), and (g) are performed wirelessly.

In an embodiment of fourth aspect, the method further comprises releasably coupling the first computing device to the second computing device, wherein electrical communication between the first computing device and the second computing device occurs upon the coupling.

In a fifth aspect, a method is provided of presenting a user interface of a continuous glucose monitoring system, comprising: selectively displaying one of a plurality of display screens on a user interface in response to user selection of a selectable icon associated with the selected display screen, the plurality of display screens comprising: a first display screen including one or more of a time indicating when sensor data received from a continuous glucose sensor was last updated, a glucose concentration trend arrow, a graph showing glucose concentration over a predetermined period of time, a maximum glucose value over the predetermined period of time, a minimum glucose value over the predetermined period of time, an average glucose value over the predetermined period of time or a deviation of glucose concentration over the predetermined period of time; a second display screen including a plurality of selectable items that, when selected, allow a user to input information using the user interface related to the selected item, the plurality of selectable items comprising one or more of a reference value item that when selected causes the user interface to prompt a user to input a reference value; a messaging item that when selected causes the user interface to prompt a user to select one of a plurality of alerts and a contact address, wherein when the selected alert is triggered the system automatically sends an alert message to the contact address; or an alert item that when selected causes the user interface to prompt a user to modify one or more alert thresholds associated with an alert; a third display screen that prompts a user to input event related information, the event related information comprising one or more of exercise information, caloric intake related information or medication dosage related information; and a fourth display screen that includes a selectable sensor start icon that, when selected, causes the continuous glucose monitoring system to initiate sensing of a continuous glucose sensor of the continuous glucose monitoring system and a selectable sensor stop icon that when selected causes the continuous glucose monitoring system to suspend sensing of the continuous glucose sensor of the continuous glucose monitoring system, wherein the user interface displays the plurality of selectable icons during display of at least some of the plurality of display screens, wherein the selectable icon associated with the first display screen includes a current glucose concentration value, wherein the user interface is incorporated into a mobile computing device having a touch sensitive display screen, wherein the user interface comprises software downloaded onto the mobile computing and executed by a processor module of the mobile computing device, and wherein the user interface allows sharing a screen with a remotely located device so the screen of the user interface is substantially the same as a screen displayed on a remotely located device.

DETAILED DESCRIPTION OF THE PREFERRED EMBODIMENT

Figure 1A:
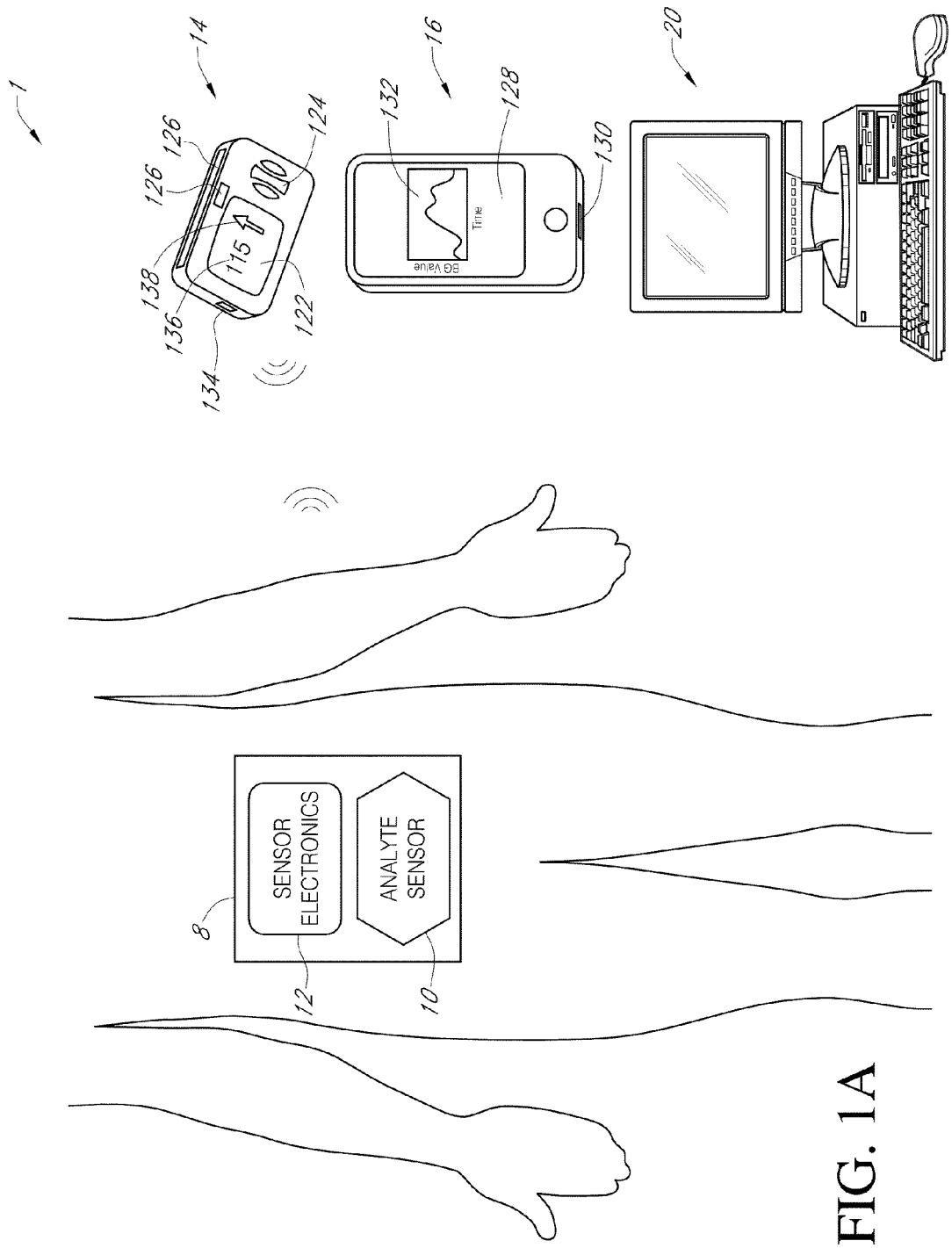
FIGS. 1A-1C are schematic diagrams of various features of a glucose monitoring system in accordance with one embodiment of the present invention.

Various aspects of implementations within the scope of the appended claims are described below. It should be apparent that the aspects described herein may be implemented in a wide variety of forms and that any specific structure and/or function described herein is merely illustrative. Based on the present disclosure a person/one having ordinary skill in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

Definitions

In order to facilitate an understanding of the systems and methods discussed herein, a number of terms are defined below. The terms defined below, as well as other terms used herein, should be construed to include the provided definitions, the ordinary and customary meaning of the terms, and any other implied meaning for the respective terms. Thus, the definitions below do not limit the meaning of these terms, but only provide exemplary definitions.

The term "analyte" as used herein is a broad term and is to be given its ordinary and customary meaning to a person of ordinary skill in the art (and is not to be limited to a special or customized meaning), and furthermore refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is analyte. However, other analytes are contemplated as well, including but not limited to a carboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica, enterovirus, Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferring; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "A/D Converter" as used herein is a broad term and is to be given its ordinary and customary meaning to a person of ordinary skill in the art (and is not to be limited to a special or customized meaning), and furthermore refers without limitation to hardware and/or software that converts analog electrical signals into corresponding digital signals.

The terms "processor module," "microprocessor" and "processor" as used herein are broad terms and are to be given their ordinary and customary meaning to a person of ordinary skill in the art (and are not to be limited to a special or customized meaning), and furthermore refer without limitation to a computer system, state machine, and the like that performs arithmetic and logic operations using logic circuitry that responds to and processes the basic instructions that drive a computer.

The terms "sensor data", as used herein is a broad term and is to be given its ordinary and customary meaning to a person of ordinary skill in the art (and are not to be limited to a special or customized meaning), and furthermore refers without limitation to any data associated with a sensor, such as a continuous analyte sensor. Sensor data includes a raw data stream, or simply data stream, of analog or digital signal directly related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as a from a substantially continuous glucose sensor, which comprises individual measurements taken at time intervals ranging from fractions of a second up to, e.g., 1, 2, or 5 minutes or longer. In another example, the sensor data includes an integrated digital value representative of one or more data points averaged over a time period. Sensor data may include calibrated data, smoothed data, filtered data, transformed data, and/or any other data associated with a sensor.

The term "calibration" as used herein is a broad term and is to be given its ordinary and customary meaning to a person of ordinary skill in the art (and is not to be limited to a special or customized meaning), and furthermore refers without limitation to a process of determining a relationship between a raw data stream and corresponding reference data, which can be used to convert raw data into calibrated data (defined below). In some embodiments, such as continuous analyte sensors, for example, calibration can be updated or recalibrated over time as changes in the relationship between the raw data and reference data occur, for example, due to changes in sensitivity, baseline, transport, metabolism, and the like.

The terms "calibrated data" and "calibrated data stream" as used herein are broad terms and are to be given their ordinary and customary meaning to a person of ordinary skill in the art (and are not to be limited to a special or customized meaning), and furthermore refer without limitation to data that has been transformed from its raw state to another state using a function, for example a conversion function, to provide a meaningful value to a user.

The terms "smoothed data" and "filtered data" as used herein are broad terms and are to be given their ordinary and customary meaning to a person of ordinary skill in the art (and are not to be limited to a special or customized meaning), and furthermore refer without limitation to data that has been modified to make it smoother and more continuous and/or to remove or diminish outlying points, for example, by performing a moving average of the raw data stream. Examples of data filters include FIR (finite impulse response), IIR (infinite impulse response), moving average filters, and the like.

The terms "smoothing" and "filtering" as used herein are broad terms and are to be given their ordinary and customary meaning to a person of ordinary skill in the art (and are not to be limited to a special or customized meaning), and furthermore refer without limitation to a mathematical computation that attenuates or normalizes components of a signal, such as reducing noise errors in a raw data stream. In some embodiments, smoothing refers to modification of a data stream to make it smoother and more continuous or to remove or diminish outlying data points, for example, by performing a moving average of the raw data stream.

The term "noise signal" as used herein is a broad term and is to be given its ordinary and customary meaning to a person of ordinary skill in the art (and is not to be limited to a special or customized meaning), and furthermore refers without limitation to a signal associated with noise on the data stream (e.g., non-analyte related signal). The noise signal can be determined by filtering and/or averaging, for example. In some embodiments, the noise signal is a signal residual, delta residual (difference of residual), absolute delta residual, and/or the like, which are described in more detail elsewhere herein.

The term "algorithm" as used herein is a broad term and is to be given its ordinary and customary meaning to a person of ordinary skill in the art (and is not to be limited to a special or customized meaning), and furthermore refers without limitation to a computational process (associated with computer programming or other written instructions) involved in transforming information from one state to another.

The term "matched data pairs" as used herein is a broad term and is to be given its ordinary and customary meaning to a person of ordinary skill in the art (and is not to be limited to a special or customized meaning), and furthermore refers without limitation to reference data (for example, one or more reference analyte data points) matched with substantially time corresponding sensor data (for example, one or more sensor data points).

The term "counts" as used herein is a broad term and is to be given its ordinary and customary meaning to a person of ordinary skill in the art (and is not to be limited to a special or customized meaning), and furthermore refers without limitation to a unit of measurement of a digital signal. In one example, a raw data stream measured in counts is directly related to a voltage (e.g., converted by an A/D converter), which is directly related to current from the working electrode. In another example, counter electrode voltage measured in counts is directly related to a voltage.

The term "sensor" as used herein is a broad term and is to be given its ordinary and customary meaning to a person of ordinary skill in the art (and is not to be limited to a special or customized meaning), and furthermore refers without limitation to any device (or portion of a device) that measures a physical quantity and converts it into a signal that can be processed by analog and/or digital circuitry. Thus, the output of a sensor may be an analog and/or digital signal. Examples of sensors include analyte sensors, glucose sensors, temperature sensors, altitude sensors, accelerometers, and heart rate sensors.

The terms "glucose sensor" as used herein is a broad term and is to be given its ordinary and customary meaning to a person of ordinary skill in the art (and are not to be limited to a special or customized meaning), and furthermore refer without limitation to any sensor by which glucose can be quantified (e.g., enzymatic or non-enzymatic). For example, some embodiments of a glucose sensor may utilize a membrane that contains glucose oxidase that catalyzes the conversion of oxygen and glucose to hydrogen peroxide and gluconate, as illustrated by the following chemical reaction:

$$Glucose + O_2 \rightarrow Gluconate + H_2O_2$$

Because for each glucose molecule metabolized, there is a proportional change in the co-reactant $O_2$ and the product $H_2O_2$, one can use an electrode to monitor the current change in either the co-reactant or the product to determine glucose concentration.

The terms "coupled", "operably connected" and "operably linked" as used herein are broad terms and are to be given their ordinary and customary meaning to a person of ordinary skill in the art (and are not to be limited to a special or customized meaning), and furthermore refer without limitation to one or more components being linked to another component(s), either directly or indirectly, in a manner that allows transmission of signals between the components. For example, modules of a computing device that communicate via a common data bus are coupled to one another. As another example, one or more electrodes of a glucose sensor can be used to detect the amount of glucose in a sample and convert that information into a signal, e.g., an electrical or electromagnetic signal; the signal can then be transmitted to an electronic circuit. In this case, the electrode is "operably linked" to the electronic circuitry, even though the analog signal from the electrode is transmitted and/or transformed by analog and/or digital circuitry before reaching the electronic circuit. These terms are broad enough to include wireless connectivity.

The term "physically connected" as used herein is a broad term and is to be given its ordinary and customary meaning to a person of ordinary skill in the art (and are not to be limited to a special or customized meaning), and furthermore refers without limitation to one or more components that are connected to another component(s) through direct contact and/or a wired connection, including connecting via one or more intermediate physically connecting component(s). For example, a glucose sensor may be physically connected to a sensor electronics module, and thus the processor module located therein, either directly or via one or more electrical connections.

The term "substantially" as used herein is a broad term and is to be given its ordinary and customary meaning to a person of ordinary skill in the art (and is not to be limited to a special or customized meaning), and furthermore refers without limitation to being largely but not necessarily wholly that which is specified.

The term "host" as used herein is a broad term and is to be given its ordinary and customary meaning to a person of ordinary skill in the art (and is not to be limited to a special or customized meaning), and furthermore refers without limitation to mammal, such as a human implanted with a device.

The term "continuous analyte sensor" as used herein is a broad term and is to be given its ordinary and customary meaning to a person of ordinary skill in the art (and is not to be limited to a special or customized meaning), and furthermore refers without limitation to a device, or portion of a device, that continuously or continually measures a concentration of an analyte, for example, at time intervals ranging from fractions of a second up to, for example, 1, 2, or 5 minutes, or longer. In one exemplary embodiment, a glucose sensor comprises a continuous analyte sensor, such as is described in U.S. Pat. No. 7,310,544, which is incorporated herein by reference in its entirety.

The term "continuous analyte sensing" as used herein is a broad term and is to be given its ordinary and customary meaning to a person of ordinary skill in the art (and is not to be limited to a special or customized meaning), and furthermore refers without limitation to the period in which monitoring of an analyte is continuously or continually performed, for example, at time intervals ranging from fractions of a second up to, for example, 1, 2, or 5 minutes, or longer. In one embodiment, a glucose sensor performs continuous analyte sensing in order to monitor a glucose level in a corresponding host.

The terms "reference analyte monitor," "reference analyte meter," and "reference analyte sensor" as used herein are broad terms and are to be given their ordinary and customary meaning to a person of ordinary skill in the art (and are not to be limited to a special or customized meaning), and furthermore refer without limitation to a device that measures a concentration of an analyte and can be used as a reference for a continuous analyte sensor, for example a self-monitoring blood glucose meter (SMBG) can be used as a reference for a continuous glucose sensor for comparison, calibration, and the like.

The term "clinical acceptability", as used herein, is a broad term and is to be given its ordinary and customary meaning to a person of ordinary skill in the art (and is not to be limited to a special or customized meaning), and refers without limitation to determination of the risk of inaccuracies to a patient. Clinical acceptability may consider a deviation between time corresponding glucose measurements (e.g., data from a glucose sensor and data from a reference glucose monitor) and the risk (e.g., to the decision making of a diabetic patient) associated with that deviation based on the glucose value indicated by the sensor and/or reference data. One example of clinical acceptability may be 85% of a given set of measured analyte values within the "A" and "B" region of a standard Clarke Error Grid when the sensor measurements are compared to a standard reference measurement.

The term "quality of calibration" as used herein, is a broad term and is to be given its ordinary and customary meaning to a person of ordinary skill in the art (and is not to be limited to a special or customized meaning), and refers without limitation to the statistical association of matched data pairs in the calibration set used to create the conversion function. For example, an R-value may be calculated for a calibration set to determine its statistical data association, wherein an R-value greater than 0.79 determines a statistically acceptable calibration quality, while an R-value less than 0.79 determines statistically unacceptable calibration quality.

The term "sensor session" as used herein, is a broad term and is to be given its ordinary and customary meaning to a person of ordinary skill in the art (and is not to be limited to a special or customized meaning), and refers without limitation to a period of time a sensor is in use, such as but not limited to a period of time starting at the time the sensor is implanted (e.g., by the host) to removal of the sensor (e.g., removal of the sensor from the host's body and/or removal of the sensor electronics module from the sensor housing).

The terms "noise," "noise event(s)," "noise episode(s)," "signal artifact(s)," "signal artifact event(s)," and "signal artifact episode(s)" as used herein are broad terms and are to be given their ordinary and customary meaning to a person of ordinary skill in the art (and are not to be limited to a special or customized meaning), and furthermore refer without limitation to signal noise that is substantially non-glucose related, such as interfering species, macro- or micro-motion, ischemia, pH changes, temperature changes, pressure, stress, or even unknown sources of mechanical, electrical and/or biochemical noise for example.

The term "measured analyte values" as used herein is a broad term and is to be given its ordinary and customary meaning to a person of ordinary skill in the art (and is not to be limited to a special or customized meaning), and furthermore refers without limitation to an analyte value or set of analyte values for a time period for which analyte data has been measured by an analyte sensor. The term is broad enough to include sensor data from the analyte sensor before or after data processing in the sensor and/or receiver (for example, data smoothing, calibration, and the like).

The term "estimated analyte values" as used herein is a broad term and is to be given its ordinary and customary meaning to a person of ordinary skill in the art (and is not to be limited to a special or customized meaning), and furthermore refers without limitation to an analyte value or set of analyte values, which have been algorithmically extrapolated from measured analyte values. In some embodiments, estimated analyte values are estimated for a time period during which no data exists. However, estimated analyte values can also be estimated during a time period for which measured data exists, but is to be replaced by algorithmically extrapolated (e.g. processed or filtered) data due to noise or a time lag in the measured data, for example.

The term "calibration information" as used herein is a broad term and is to be given its ordinary and customary meaning to a person of ordinary skill in the art (and is not to be limited to a special or customized meaning), and furthermore refers without limitation to any information useful in calibration of a sensor. Calibration information may include reference data received from a reference analyte monitor, including one or more reference data points, one or more matched data pairs formed by matching reference data (e.g., one or more reference glucose data points) with substantially time corresponding sensor data (e.g., one or more continuous sensor data points), a calibration set formed from a set of one or more matched data pairs, a calibration line drawn from the calibration set, in vitro parameters (e.g., sensor sensitivity), and/or a manufacturing code, for example.

The term "alarm" as used herein is a broad term, and is to be given its ordinary and customary meaning to a person of ordinary skill in the art (and is not to be limited to a special or customized meaning), and furthermore refers without limitation to an alert or signal, such as an audible, visual, or tactile signal, triggered in response to one or more alarm conditions. In one embodiment, hyperglycemic and hypoglycemic alarms are triggered when present or predicted clinical danger is assessed based on continuous analyte data.

The term "transformed sensor data" as used herein is a broad term, and is to be given its ordinary and customary meaning to a person of ordinary skill in the art (and is not to be limited to a special or customized meaning), and furthermore refers without limitation to any data that is derived, either fully or in part, from raw sensor data from one or more sensors. For example, raw sensor data over a time period (e.g., 5 minutes) may be processed in order to generated transformed sensor data including one or more trend indicators (e.g., a 5 minute trend). Other examples of transformed data include filtered sensor data (e.g., one or more filtered analyte concentration values), calibrated sensor data (e.g., one or more calibrated analyte concentration values), rate of change information, trend information, rate of acceleration information, sensor diagnostic information, location information, alarm/alert information, calibration information, and/or the like.

The term "sensor information" as used herein is a broad term, and is to be given its ordinary and customary meaning to a person of ordinary skill in the art (and is not to be limited to a special or customized meaning), and furthermore refers without limitation to information associated with measurement, signal processing (including calibration), alarms, data transmission, and/or display associated with a sensor, such as a continuous analyte sensor. The term is broad enough to include raw sensor data (one or more raw analyte concentration values), as well as transformed sensor data. In some embodiments, sensor information includes displayable sensor information.

The term "displayable sensor information" as used herein is a broad term, and is to be given its ordinary and customary meaning to a person of ordinary skill in the art (and is not to be limited to a special or customized meaning), and furthermore refers without limitation to information that is transmitted for display on one or more display devices. As is discussed elsewhere herein, the content of displayable sensor information that is transmitted to a particular display device may be customized for the particular display device. Additionally, formatting of displayable sensor information may be customized for respective display devices. Displayable sensor information may include any sensor data, including raw sensor data, transformed sensor data, and/or any information associated with measurement, signal processing (including calibration), and/or alerts associated with one or more sensors.

The term "data package" as used herein is a broad term, and is to be given its ordinary and customary meaning to a person of ordinary skill in the art (and is not to be limited to a special or customized meaning), and furthermore refers without limitation to a combination of data that is transmitted to one or more display devices, such as in response to triggering of an alert. A data package may include displayable sensor information (e.g., that has been selected and formatted for a particular display device) as well as header information, such as data indicating a delivery address, communication protocol, etc. Depending on the embodiment, a data package may comprises multiple packets of data that are separately transmitted to a display device (and reassembled at the display device) or a single block of data that is transmitted to the display device. Data packages may be formatted for transmission via any suitable communication protocol, including radio frequency, Bluetooth, universal serial bus, any of the wireless local area network (WLAN) communication standards, including the IEEE 802.11, 802.15, 802.20, 802.22 and other 802 communication protocols, and/or a proprietary communication protocol.

The term "direct wireless communication" as used herein is a broad term, and is to be given its ordinary and customary meaning to a person of ordinary skill in the art (and is not to be limited to a special or customized meaning), and furthermore refers without limitation to a data transmission that goes from one device to another device without any intermediate data processing (e.g., data manipulation). For example, direct wireless communication between a sensor electronics module and a display device occurs when the sensor information transmitted from the sensor electronics module is received by the display device without intermediate processing of the sensor information. The term is broad enough to include wireless communication that is transmitted through a router, a repeater, a telemetry receiver (e.g., configured to re-transmit the sensor information without additional algorithmic processing), and the like. The term is also broad enough to include transformation of data format (e.g., via a Bluetooth receiver) without substantive transformation of the sensor information itself.

The term "prospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in real-time (e.g., continuously and/or periodically as sensor data is received from the continuous analyte sensor) and provide real-time data output (e.g., continuously and/or periodically as sensor data is processed in the sensor electronics module).

The term "retrospective algorithm(s)" as used herein is a broad term, and is to be given its ordinary and customary meaning to a person of ordinary skill in the art (and is not to be limited to a special or customized meaning), and furthermore refers without limitation to algorithms that process sensor information in retrospect, (e.g., analysis of a set of data for a time period previous to the present time period).

As employed herein, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade).

Overview of a Receiver/Display Device Configuration

In some embodiments, a system is provided for continuous measurement of an analyte in a host that includes: a continuous analyte sensor configured to continuously measure a concentration of the analyte in the host, a sensor electronics module coupled to the continuous analyte sensor during sensor use and a receiver unit in wireless communication with the sensor electronics module. The receiver unit can include electronics configured to process sensor data received from the sensor electronics module and display or otherwise communicate (e.g., via audible communication) sensor-related information to a user.

In one embodiment, the receiver unit is a computer processor-based device that can be physically and electrically coupled to a secondary display device having a larger display, such as a mobile telephone, personal digital assistant (PDA), MP3 player or the like. The receiver unit can include a housing shaped to mechanically couple the receiver unit to the secondary computer device and a communication port configured to electrically couple the receiver unit with the secondary computer device. In one exemplary embodiment, the housing of the receiver unit includes an opening shaped to enclose a portion of a secondary display device, such as an end of a mobile telephone, or shaped to enclose a bottom and one or more sides of a mobile telephone, and physically connect the communication port of the receiving unit to a corresponding communication port of the secondary display device.

In one embodiment, the receiver unit is designed to have limited functionality. For example, the receiver unit can include a limited user interface consisting of a small display that is configured to display limited information, such as a recently measured analyte concentration value and a trend arrow. In other examples, the user interface can also include an audible alarm, a vibrator motor alarm, and two or three input buttons. The input buttons can be used to input information into the receiver unit such as reference calibration information used to calibrate a sensor (e.g., glucose concentration values from a single point blood glucose monitor) or alarm settings. By keeping the functionality of the receiver unit limited, the receiver unit can be easily carried by the user, yet provide the user with important information and alerts without the need of a larger, secondary computing device. In addition, the receiver unit can be coupled to a secondary display device to display enhanced sensor related information that a user may want to view, such as detailed reports based on a retrospective analysis of sensor data.

When coupled to the receiver unit, the secondary display device can also be used to modify user-configurable settings of the receiver unit and input various types of information into the receiver unit, such as reference calibration values. Accordingly, when a user wants to carry only a small device and does not need expansive display and user input capabilities, the user need only carry the receiver unit. In contrast, when the user does not mind carrying a larger display device and/or wants to have enhanced display and/or user input capabilities, the user can simply couple the receiver unit to a secondary display device.

Alerts

In one embodiment, one or more alerts are associated with a receiver unit and/or sensor electronics module. For example, each alert may include one or more alert conditions that indicate when the respective alert has been triggered. For example, a hypoglycemic alert may include alert conditions indicating a minimum glucose level. The alert conditions may also be based on transformed sensor data, such as trending data, and/or sensor data from multiple different sensors (e.g. an alert may be based on sensor data from both a glucose sensor and a temperature sensor). For example, a hypoglycemic alert may include alert conditions indicating a minimum required trend in the host's glucose level that must be present before triggering the alert. The term "trend," as used herein refers generally to data indicating some attribute of data that is acquired over time, e.g., such as calibrated or filtered data from a continuous glucose sensor. A trend may indicate amplitude, rate of change, acceleration, direction, etc., of data, such as sensor data, including transformed or raw sensor data.

In one embodiment, each of the alerts is associated with one or more actions that are to be performed in response to triggering of the alert. Alert actions may include, for example, activating an alarm, such as displaying information on a display of the sensor electronics module or receiver unit, or activating an audible or vibratory alarm coupled to the sensor electronics module or receiving unit, and/or transmitting data to one or more display devices (e.g., computer devices) external to the receiver unit.

In one embodiment, multiple delivery actions (each having respective delivery options) may be associated with a single alert such that displayable sensor information having different content and formatting, for example, is transmitted to respective receiver unit and secondary display devices in response to triggering of a single alert. For example, a mobile telephone may receive a data package including minimal displayable sensor information (that may be formatted specifically for display on the mobile telephone), while a desktop computer may receive a data package including most (or all) of the displayable sensor information that is generated by the sensor electronics module and/or receiver module in response to triggering of a common alert. Advantageously, the sensor electronics module need not be tied to a single display device, rather it can configured to communicate with a plurality of different display devices directly, systematically, simultaneously (e.g., via broadcasting), regularly, periodically, randomly, on-demand, in response to a query, based on alerts or alarms, and/or the like. Further details related to communicating with a plurality of different displays is described in more detail in U.S. Patent Publication No. 2009/0240120 entitled "Systems and Methods for Processing, Transmitting and Displaying Sensor Data" and filed on Feb. 20, 2009, the content of which is incorporated herein by reference in its entirety.

In some embodiments, clinical risk alerts are provided that include alert conditions that combine intelligent and dynamic estimative algorithms that estimate present or predicted danger with greater accuracy, more timeliness in pending danger, avoidance of false alarms, and less annoyance for the patient. In general, clinical risk alerts include dynamic and intelligent estimative algorithms based on analyte value, rate of change, acceleration, clinical risk, statistical probabilities, known physiological constraints, and/or individual physiological patterns, thereby providing more appropriate, clinically safe, and patient-friendly alarms. U.S. Patent Publication No. 2007/0208246, which is incorporated herein by reference in its entirety, describes some systems and methods associated with the clinical risk alerts (or alarms) described herein. In some embodiments, clinical risk alerts can be triggered for a predetermined time period to allow for the user to attend to his/her condition. Additionally, the clinical risk alerts can be de-activated when leaving a clinical risk zone so as not to annoy the patient by repeated clinical alarms (e.g., visual, audible or vibratory), when the patient's condition is improving. In some embodiments, dynamic and intelligent estimation determines a possibility of the patient avoiding clinical risk, based on the analyte concentration, the rate of change, and other aspects of the dynamic and intelligent estimative algorithms. If there is minimal or no possibility of avoiding the clinical risk, a clinical risk alert will be triggered. However, if there is a possibility of avoiding the clinical risk, the system can be configured to wait a predetermined amount of time and re-analyze the possibility of avoiding the clinical risk. In some embodiments, when there is a possibility of avoiding the clinical risk, the system is further configured to provide targets, therapy recommendations, or other information that can aid the patient in proactively avoiding the clinical risk.

In some embodiments, the sensor electronics module is configured to search for one or more devices (e.g., receiver unit or secondary display device) within communication range of the sensor electronics module and to wirelessly communicate sensor information (e.g., a data package including displayable sensor information, one or more alarm conditions, and/or other alarm information) thereto. Accordingly, the device(s) can be configured to display at least some of the sensor information and/or alarm the host (and/or care taker), wherein the alarm mechanism is located on the device. The device(s) can also be configured to repeat the sensor information to one or more additional devices.

In some embodiments, the receiver unit and/or sensor electronics module is configured to provide one or a plurality of different alarms via the respective receiver unit or sensor electronics module and/or via transmission of a data packaging indicating an alarm should be initiated by one or a plurality of secondary display devices (e.g., sequentially and/or simultaneously). In some embodiments, the receiver unit determines which of the one or more alarms to trigger based on one or more alerts that are triggered. For example, when an alert triggers that indicates severe hypoglycemia, the receiver unit can perform multiple actions, such as activating an alarm on the receiver unit, transmitting a data package to a remote display device indicating activation of an alarm on the display, and transmitting a data package as a text message to a care provider. As an example, a text message can appear on a small (e.g., key fob) display, cell phone, pager device, and/or the like, including displayable sensor information that indicates the host's condition (e.g., "severe hypoglycemia").

In some embodiments, the sensor electronics module is configured to directly, systematically, simultaneously (e.g., via broadcasting), regularly, periodically, randomly, on-demand, in response to a query (from the receiver unit), based on alerts or alarms, and/or the like transmit alarm information. In some embodiments, the receiver unit can function as a repeater such that the wireless communication distance of the sensor electronics module can be increased, for example, to 10, 20, 30, 50 75, 100, 150, or 200 meters or more, wherein the receiver unit is configured to repeat a wireless communication from the sensor electronics module to a display device located remotely from the sensor electronics module. A receiver unit functioning as a repeater can be useful to families having children with diabetes. For example, to allow a parent to carry, or place in a stationary position, a display device, such as in a large house wherein the parents sleep at a distance from the child.

In some embodiments, the receiver unit 14 can also receive sensor data from the sensor electronics module 8 in a first communication format and repeat the sensor data to secondary display unit 16 or 20 in a second, different communication formation. As an example, the sensor electronics module 8 may be configured to transmit sensor-related information using a first wireless communication protocol. The receiver unit 14 can receive the communication from the sensor electronics module 8, process the information and re-transmit wirelessly or via a wired connection some or all of the sensor related-information using a second, different protocol. In this way, a display device that does not have the functionality to receive and process information using the first communication protocol can receive the sensor-related information using the second protocol via the receiver unit 14.

Display Devices

In some embodiments, the sensor electronics module 8 and/or the receiver unit 14 can communicate with a variety of display devices, such as secondary display devices 16 and 20 illustrated in FIG. 1A, via wireless or wired transmission. One or more of the display device that receive data packages from the sensor electronics module 8 or receiver unit 14 can be "dummy displays", wherein they display the displayable sensor information received from the sensor electronics module 8 or receiver unit 14 without additional processing (e.g., prospective algorithmic processing necessary for real-time display of sensor information). The displayable sensor information comprises transformed sensor data that does not require processing by the display device prior to display of the displayable sensor information. Some display devices may comprise software including display instructions (software programming comprising instructions configured to display the displayable sensor information and optionally query the receiver unit to obtain the displayable sensor information) configured to enable display of the displayable sensor information thereon. The display device can be programmed with the display instructions at the manufacturer and can include security and/or authentication to avoid plagiarism of the display device or the display device can be configured to display the displayable sensor information via a downloadable program (for example, an application via the internet, such as an iTunes App via Apple Inc.'s online iTunes store), such that any display device that supports downloading of a program (for example, any display device that supports Java applets) therefore can be configured to display displayable sensor information (e.g., mobile phones, PDAs, tablet computers, PCs and the like).

In one embodiment, the receiver unit 14 comprises a built-in authentication mechanism, but a secondary display device coupled to the receiver unit does not, wherein authentication is required for communication with the sensor electronics module 8. In this regard, the receiver unit 14 can function as an intermediary device that communicates with the sensor electronics module 8 and also provides displayable sensor data, for example to the display device. In some embodiments, to authenticate the data communication between the sensor electronics module and display devices, a challenge-response protocol, such as a password authentication is provided, where the challenge is a request for the password and the valid response is the correct password, such that pairing of the sensor electronics module with the receiver unit can be accomplished by the user and/or manufacturer via the password. However, any known authentication system or method useful for telemetry devices can be used with the preferred embodiments.

In some embodiments, the receiver unit 14 is configured to query the sensor electronics module 8 for sensor data, wherein the receiver unit acts as a master device requesting sensor data from the sensor electronics module (e.g., a slave device) on-demand, for example, in response to a query. In some embodiments, the sensor electronics module is configured for periodic, systematic, regular, and/or periodic transmission of sensor information to a receiver unit and/or one or more display devices (for example, every 1, 2, 5, or 10 minutes or more). In some embodiments, the sensor electronics module 8 is configured to transmit data packages associated with a triggered alert (e.g., triggered by one or more alert conditions). However, any combination of the above described statuses of data transmission can be implemented with any combination of paired sensor electronics module 8, receiver unit 14 and display device(s). For example, the receiver unit 14 and one or more display devices can each be configured for querying the sensor electronics module database and for receiving alarm information triggered by one or more alarm conditions being met. Additionally, the sensor electronics module can be configured for periodic transmission of sensor information to the receiver unit and one or more display devices (the same or different display devices as described in the previous example), whereby a system can include devices that function differently with regard to how they obtain sensor information.

In some embodiments, as described in more detail elsewhere herein, the receiver unit 14 is configured to query the data storage memory in the sensor electronics module 8 for certain types of data content, including direct queries into a database in the sensor electronics module's memory and/or requests for configured or configurable packages of data content therefrom; namely, the data stored in the sensor electronics module 8 is configurable, queryable, predetermined, and/or pre-packaged, based on the display device with which the sensor electronics module is communicating. In some additional or alternative embodiments, the sensor electronics module 8 generates the displayable sensor information based on its knowledge of which display device is to receive a particular transmission. Additionally, receiver unit 14 may be capable of obtaining calibration information and wirelessly transmitting the calibration information to the sensor electronics module 8, such as through manual entry of the calibration information, automatic delivery of the calibration information, and/or an integral reference analyte monitor incorporated into the receiver unit. U.S. Patent Publication Nos.2006/0222566, 2007/0203966, 2007/0208245, and 2005/0154271, all of which are incorporated herein by reference in their entirety, describe systems and methods for providing an integral reference analyte monitor incorporated into an electronics device and/or other calibration methods that can be implemented with the disclosed embodiments.

In general, a receiver unit 14 (e.g., a small display device) is configured to wirelessly communicate with the sensor electronics module 8 and one or more secondary display devices (e.g., a larger display device, a larger (hand-held) display device, a mobile phone, a reference analyte monitor, a drug delivery device, a medical device and a personal computer). The receiver unit 14 can be configured to display at least some of the displayable sensor information either wirelessly communicated from the sensor electronics module 8 or processed in the receiver unit, wherein displayable sensor information includes sensor data, such as raw data and/or transformed sensor data, such as analyte concentration values, rate of change information, trend information, alert information, sensor diagnostic information and/or calibration information, for example. In addition, the secondary devices can be configured to display displayable sensor information communicated from the receiver unit when physically coupled to the receiver unit.

Receiver Unit

An exemplary configuration of a receiver unit 14 in accordance with one embodiment is illustrated in FIG. 1A. The receiver unit 14 FIG. can be configured to display sensor information on a display 122, such as an analyte concentration value 136 and a trend arrow 138. An exemplary receiver unit 14 can be in the form of a small hardware device that is mechanically removably attachable to a communication port of a larger hand-held computing device 16 (e.g., mobile telephone).

Figure 1B:
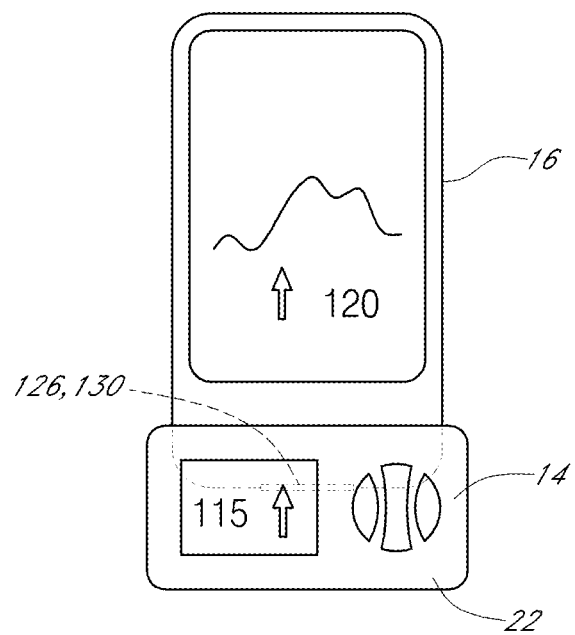
Figure 1C:
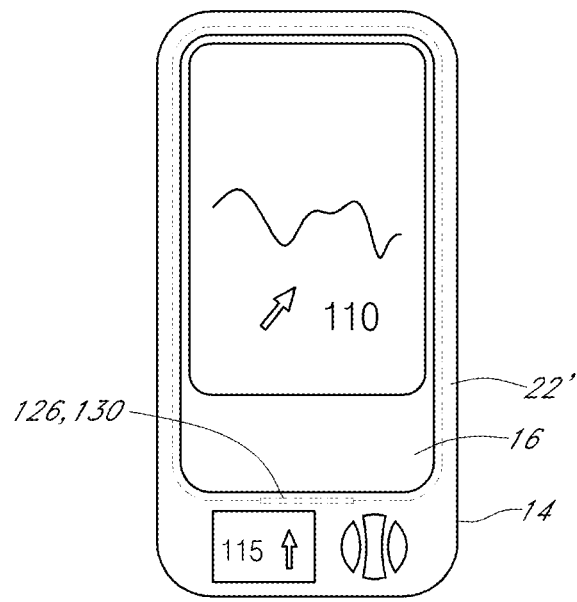

However, receiver unit 14 can have a variety of different shaped and sized housings, the shapes and sizes optionally selected to make the receiver unit 14 easy and convenient to carry when alone and/or when the receiver unit is attached to a hand-held secondary display device. Other exemplary configurations of the receiver unit 14 include: a housing 22 having an opening shaped to enclose an end portion of a housing of the hand-held computing device 16 (FIG. 1B); and a housing 22' configured to substantially enclose a bottom and sides of a hand-held secondary display device 16 (FIG. 1C). Respective communication ports 130, 134 of the secondary display device 16 and receiver unit 14 can be physically coupled when the receiver unit 14 is physically attached to the secondary display device 16 to allow for wired communication between the devices. Further exemplary configurations of the receiver unit 14 include a key fob with a USB (Universal Serial Bus) port at one end, a wrist band, a wrist watch, a hang tag, a belt, a necklace, a pendent, a piece of jewelry, an adhesive patch, a pager, an identification (ID) card, and the like.

Referring back to FIG. 1A, the receiver unit 14 can be a small electronics device in accordance with some embodiments, where the receiver unit 14 comprises a relatively small display 122 (e.g., smaller than the display 128 of the secondary display device 16) and is configured to display certain types of displayable sensor information (e.g., only a numerical value 136 and an arrow 138).

In general, the receiver unit 14 can include electronics configured to receive and display sensor information (and optionally configured to query a sensor electronics module for the sensor information). In one embodiment, the electronics include a RAM and a program storage memory configured at least to display the sensor data received from the sensor electronics module. In some embodiments, the receiver unit 14 includes an alarm configured to warn a host of a triggered alert (e.g., audio, visual and/or vibratory). In some embodiments, the receiver unit 14 includes a user interface, such as a liquid crystal display (LCD) 122 and one or more buttons 124 that allow a user to view data, such as a numeric value and/or an arrow, to toggle through one or more screens, to select or define one or more user parameters, to respond to (e.g., silence, snooze, turn off) an alert, and/or the like.

In some embodiments, the receiver unit 14 has a memory (e.g., such as in a gig stick or thumb drive) that stores sensor, drug (e.g., insulin) and other medical information, enabling a memory stick-type function that allows data transfer from the sensor electronics module to another device (e.g., a mobile telephone or PC) and/or as a data back-up location for the sensor electronics module memory (e.g., data storage memory). In some embodiments, the receiver unit 14 is configured to be automatically readable by a network system upon entry into a hospital or other medical complex via automatic wireless transmission, for example.

In some embodiments, the receiver unit 14 includes a first data port 134, to enable connection to a corresponding port on a computing device (e.g., mobile telephone), enabling the receiver unit to function as a data download device (e.g., from the sensor electronics module to a PC), a telemetry connector (e.g., Bluetooth adapter/connector for a PC), and/or enables user to configure settings on the receiver unit (e.g., via software on the PC that allows configurable parameters such as numbers, arrows, trend, alarms, font, etc.) In some embodiments, user parameters associated with the receiver unit 14 can be programmed into (and/or modified) by a display device such secondary device 16, personal computer 20, personal digital assistant, or the like. In one embodiment, user parameters include contact information, alert/alarms settings (e.g., thresholds, sounds, volume, and/or the like), calibration information, font size, display preferences, defaults (e.g., screens), and/or the like.

Alternatively, the receiver unit 14 can be configured for direct programming of user parameters. In some embodiments, wherein the receiver unit 14 comprises a telemetry module, such as Bluetooth, and a data port 130 of secondary display device 16 (such that the receiver unit additionally functions as telemetry adapter enabling wireless communication between the sensor electronics module and the computing device, for example, wherein the secondary display device does not include the capability to communicate with sensor electronics module directly, for example, because the secondary display device does not include the appropriate authentication or adapter to communicate with the electronics module.

In some embodiments, the receiver unit 14 is configured to wirelessly communicate sensor diagnostic information to a drug delivery device in order to enable to the drug delivery device to consider (include in its calculations/algorithms) a quality, reliability and/or accuracy of sensor information for closed loop and/or semi-closed loop systems, which are described in more detail in U.S. Patent Publication No. 2005/0192557, which is incorporated herein by reference in its entirety. In some alternative embodiments, the receiver unit 14 is configured to wirelessly communicate with a drug delivery device that does not include a display, for example, in order to enable a closed loop and/or semi-closed loop system as described above.

In some embodiments, one or more computing devices, such as secondary display device 16 or PC 20, can be configured for displaying (and/or alarming) displayable sensor information that has been transmitted by the receiver unit 14 (e.g., in a data package that is transmitted to the secondary display device). For example, the display device 16 or 20 can be configured to display displayable sensor information as it is communicated from the sensor electronics module (e.g., in a data package that is transmitted to respective display devices), without any additional prospective processing required for calibration and real-time display of the sensor data.

In some embodiments, the receiver unit 14 incorporates a reference analyte monitor, such as a single point blood glucose meter, configured to measure a reference analyte value associated with an analyte concentration in a biological sample from the host. A reference analyte meter port 134 can be included in the receiver unit 14 configured to receive an analyte test strip, as illustrated in FIG. 1A.

In some embodiments the receiver unit 14 has a set of configurable alert settings, wherein the set of alert settings can be initially set to a first, configuration (such as a default configuration set by a manufacturer), but modified to a second, different configuration. Display device 16 or 20 can receive user input via a user interface (e.g., via one or more buttons, a keypad, voice recognition software, touch-sensitive display, etc. incorporated into the display device) indicative of modifying the alert settings and send a data message to the receiver unit 14 indicative of the modifications. Alternatively, the receiver unit 14 can allow a user to modify the alert setting using the user interface of the receiver unit. The receiver unit 14 can then modify the current settings according to the user input. The set of settings can include a hypoglycemic setting, a hyperglycemic setting, a rate-of-change setting and a calibration setting. The receiver unit 14 can also be configured to automatically reset the set of settings to a default configuration upon the detection of a predetermined event. The predetermined event can be an indication of a data corruption error, low power indication, or a device hacking indication determined by, for example, the receiver unit 14 based on monitoring transmissions received by the receiver unit.

Secondary Display Device

With further reference to FIG. 1A, the secondary display device 16 can be a hand-held computing device configured to display sensor information including an analyte concentration and a graphical representation of the analyte concentration over time. As discussed above, in some embodiments, the receiver unit 14 can be configured to physically releasably couple with the housing of the secondary display device 16, wherein respective ports 134 and 130 of the receiver unit 14 and the display device 16 physically connect to enable direct wired communication between the receiver unit and the secondary display device.

The secondary display device 16 can include a display 128 sufficiently large to display a graphical representation 132 of the sensor data over a time period, such as a previous 1, 3, 5, 6, 9, 12, 18, or 24-hours of sensor data. The secondary display device 16 can be configured to display a trend graph or other graphical representation, a numeric value, an arrow, and/or to alarm the host. Further, the secondary display device 16 can include software installed into memory of the display device 16, wherein the software enables display and/or performs data analysis (retrospective processing) of the historic sensor information. U.S. Patent Publication No. 2005/0203360, which is incorporated herein by reference in its entirety, describes and illustrates some examples of display of data that can be performed on display device 16. The software can be downloaded over the Internet or can be uploaded automatically from the receiver unit upon initial coupling via initiation of wireless communication or physical coupling of respective data ports of the receiver 14 unit to the secondary display device 16.

Although FIG. 1A illustrates one embodiment of a secondary display device 16, the secondary display device can be any single application device or multi-application device, such as mobile phone, a palm-top computer, a PDA, portable media player (e.g., iPod, MP3 player), lap top computer, tablet computer (e.g., iPad), a blood glucose meter, an insulin pump, and/or the like.

In some embodiments, a mobile phone is configured to display (as described above) and/or relay sensor information, such as via a voice or text message, to a further secondary display device, such as another mobile phone, tablet computer, PC and the like. The further secondary display device can belong for example to a person associated with the user, such as the host's parent, spouse or care provider. In some embodiments, the mobile phone further comprises an alarm configured to warn a host of a triggered alert, such as in response to receiving an alert sent from the receiver unit 14. Depending on the embodiment, the alert can include a data package having displayable sensor information, such as an on-screen message, text message, and/or pre-generated graphical representation of sensor data and/or transformed sensor data, as well as an indication of an alarm, such as an auditory alarm or a vibratory alarm, that should be activated by the mobile phone.

In some embodiments, the secondary display device 16 is configured to communicate sensor diagnostic information to the drug delivery device in order to enable to the drug delivery device to consider (include in its calculations/algorithms) a quality, reliability and/or accuracy of sensor information for closed loop and/or semi-closed loop systems, which are described in more detail in U.S. Patent Publication No. 2005/0192557, which is incorporated herein by reference in its entirety. In some alternative embodiments, the secondary display device 16 is configured to communicate with a drug delivery device that does not include a display, for example, in order to enable a closed loop and/or semi-closed loop system as described above.

In some embodiments, the secondary display device 16 is a reference analyte monitor or incorporates a reference analyte monitor, such as a blood glucose meter, configured to measure a reference analyte value associated with an analyte concentration in a biological sample from the host.

Exemplary Configurations

Further to the monitoring system illustrated in FIG. 1A, the monitoring system 1 can include a continuous analyte sensor 10 physically connected to and in electrical communication with sensor electronics module 8. The sensor electronics module 8 can be in direct wireless communication with receiver unit 14.

In one embodiment, the sensor electronics module 8 includes electronic circuitry 12 associated with measuring and processing continuous analyte sensor data from an analyte sensor 10, including prospective algorithms associated with processing and calibrating sensor data. The sensor electronics 12 may be physically connected to the analyte sensor 10 and can be integral with (non-releasably attached to) or releasably attachable to the continuous analyte sensor 10. The sensor electronics 12 may include hardware, firmware, and/or software that enables measurement of levels of the analyte via a glucose sensor, such as an analyte sensor. For example, the sensor electronics 12 can include a potentiostat, a power source for providing power to the sensor, other components useful for signal processing and data storage, and preferably a telemetry module for transmitting and receiving data between the sensor electronics module and one or more computing devices. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The sensor electronics 12 includes sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entirety.

Continuous Sensor

In some embodiments, analyte sensor 10 comprises a continuous glucose sensor, for example a subcutaneous, transdermal (e.g., transcutaneous), or intravascular continuous glucose sensor. In some embodiments, the analyte sensor 10 can analyze a plurality of intermittent blood samples. The analyte sensor 10 can use any method of glucose-measurement, including enzymatic, chemical, physical, electrochemical, spectrophotometric, polarimetric, calorimetric, iontophoretic, radiometric, immunochemical, and the like.

Analyte sensor 10 can use any known method, including invasive, minimally invasive, and non-invasive sensing techniques (e.g., fluorescent monitoring), to provide a data stream indicative of the concentration of the analyte in a host. The data stream is typically a raw data signal, which is converted into a calibrated and/or filtered data stream that is used to provide a useful value of analyte concentration to a user, such as a patient or a caretaker (e.g., a parent, a relative, a guardian, a teacher, a doctor, a nurse, or any other individual that has an interest in the wellbeing of the host).

The analyte sensor 10 can be any device capable of measuring the concentration of an analyte. One exemplary embodiment is described below, which utilizes an implantable glucose sensor. However, it should be understood that the devices and methods described herein can be applied to any device capable of detecting a concentration of glucose and providing an output signal that represents the concentration of glucose.

In one embodiment, the analyte sensor 10 is an implantable glucose sensor, such as described with reference to U.S. Pat. No. 6,001,067 and U.S. Patent Publication No. US-2005-0027463-A1. In another embodiment, the analyte sensor 10 is a transcutaneous glucose sensor, such as described with reference to U.S. Patent Publication No. US-2006-0020187-A1. In still other embodiments, the sensor 10 is configured to be implanted in a host vessel or extracorporeally, such as is described in U.S. Patent Publication No. US-2007-0027385-A1, co-pending U.S. patent application Ser. No. 11/543,396 filed Oct. 4, 2006, co-pending U.S. patent application Ser. No. 11/691,426 filed on Mar. 26, 2007, and co-pending U.S. patent application Ser. No. 11/675,063 filed on Feb. 14, 2007. In one alternative embodiment, the sensor 10 comprises a transcutaneous sensor such as described in U.S. Pat. No. 6,565,509 to Say et al., for example. In another alternative embodiment, the sensor 10 comprises a subcutaneous sensor such as described with reference to U.S. Pat. No. 6,579,690 to Bonnecaze et al. or U.S. Pat. No. 6,484,046 to Say et al., for example. In another alternative embodiment, the sensor 10 comprises a refillable subcutaneous sensor such as described with reference to U.S. Pat. No. 6,512,939 to Colvin et al., for example. In another alternative embodiment, the sensor 10 comprises an intravascular sensor such as described with reference to U.S. Pat. No. 6,477,395 to Schulman et al., for example. In another alternative embodiment, the sensor 10 comprises an intravascular sensor such as described with reference to U.S. Pat. No. 6,424,847 to Mastrototaro et al., for example.

Exemplary Receiver Unit Electronics

Figure 2:
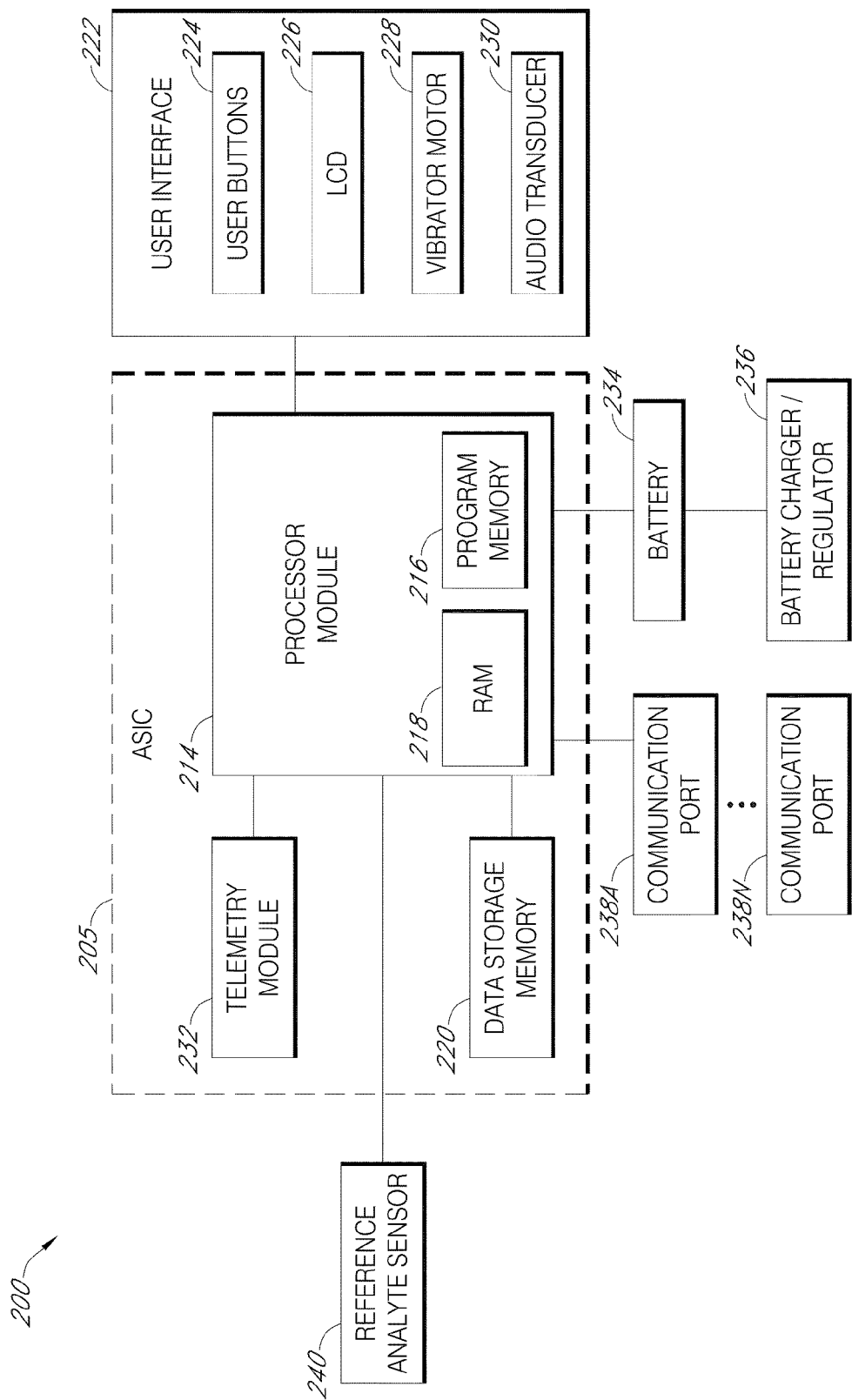
FIG. 2 is a block diagram of a receiver electronics module in accordance with one embodiment of the present invention.

FIG. 2 is a block diagram illustrating an exemplary receiver electronics module 200. Receiver electronics module 200 can be incorporated in the receiver unit 14 of FIG. 1A. In the embodiment of FIG. 2, the receiver electronics module 200 comprises an application-specific integrated circuit (ASIC) 205 and a user interface 222. In this embodiment, the ASIC 205 is coupled to a communication port 238 and a battery 234. Although the illustrated embodiment shows an Application Specific Integrated Circuit (ASIC) 205 that includes much of the electronic circuitry, the ASIC 205 may be replaced with one or more of any suitable logic device, such as field programmable gate arrays (FPGA), microprocessors, analog circuitry, or other digital and/or analog circuitry.

Processor module 214 is a central control unit that controls the processing of the receiver electronics module 200. In some embodiments, the processor module 214 is formed as part of a custom chip, such as an ASIC, however a computer system other than an ASIC can be used to process data as described herein, for example a microprocessor can be used for some or all of the sensor electronics module processing. The processor module 214 typically provides a program memory 216, which provides semi-permanent storage of data, for example, storing data such as data archived sensor data and programming to process sensor data streams (for example, filtering, calibration, fail-safe checking, and the like). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, RAM 218 can be used for the system's cache memory, for example for temporarily storing recent sensor data.

In one embodiment, the processor module 214 may be further configured to generate data packages for transmission to one or more display devices. Furthermore, the processor module 215 may generate data packets for transmission to these outside sources, e.g., via telemetry. As discussed above, the data packages may be customizable for each display device, for example, and may include any available data, such as displayable sensor information having customized sensor data and/or transformed sensor data, sensor/sensor electronics module ID code, raw data, filtered data, calibrated data, rate of change information, trend information, error detection or correction, and/or the like.

A data storage memory 220 is operably connected to the processor module 214 and is configured to store a variety of sensor information. In some embodiments, the data storage memory stores 1, 3, 4, 5, 6, 7, 8, 9, 10, 11, 12, 13, 14, 15, 20, 30 or more days of continuous analyte sensor data. In some embodiments, the data storage memory 220 stores sensor information such as raw sensor data (one or more raw analyte concentration values), calibrated data, filtered data, transformed sensor data, and/or any other displayable sensor information.

In some embodiments, receiver electronics module 200 is configured to receive and store contact information in the data storage memory (and/or program memory), including a phone number and/or email address for the sensor's host and/or health care providers for the host (e.g., family member (s), nurse(s), doctor(s), or other health care provider(s)), which enables communication with a contact person (e.g., via phone, pager and/or text messaging in response to an alarm (e.g., a hypoglycemic alarm that has not been responded to by the host)). In some embodiments, user parameters can be programmed into (and/or modified in) the data storage memory (and/or program memory) of the receiver electronics module 200, via secondary display device 16, personal computer 20, personal digital assistant, or the like. Preferably, user parameters include contact information, alert/alarms settings (e.g., thresholds, sounds, volume, and/or the like), calibration information, font size, display preferences, defaults (e.g., screens), and/or the like. Alternatively, the receiver electronics module 200 can be configured for direct programming of certain user parameters using, for example, user buttons 224.

In one embodiment, clinical data of a medical practitioner may be uploaded to the receiver electronics module 200 and stored on the data storage memory 220, for example. Thus, information regarding the host's condition, treatments, medications, etc., may be stored on the receiver electronics module 200 and may be viewable by the host or other authorized user. In one embodiment, certain of the clinical data may be included in a data package that is transmitted to secondary display device 612 in response to triggering of an alert. The clinical data may be uploaded to the receiver electronics module 200 via any available communication protocol, such as direct transmission via a wireless Bluetooth, ANT, infrared, or RF connection, or via a wired USB connection, for example. Additionally, the clinical data may be uploaded to the receiver electronics module 200 via indirect transmission, such as via one or more networks (e.g.,. local area, personal area, or wide area networks, or the Internet) or via a repeater device that receives the clinical data from a device of the medical practitioner and retransmits the clinical data to the sensor electronics module.

Although separate data storage and program memories are shown in FIG. 2, one skilled in the art appreciates a variety of configurations, including one or multiple memories that provide the necessary storage space to support the receiver electronics module 200 data processing and storage requirements. Accordingly, the described location of storage of any particular information and/or or programming is not meant to be limiting, but rather exemplary.

In some embodiments, the receiver electronics module 200 and/or sensor electronics unit 12 (FIG. 1A) is configured to perform smoothing and/or filtering algorithms on the sensor data (e.g., raw data stream and/or other sensor information), wherein the smoothed and/or filtered data is stored in the data storage memory as transformed data. Co-pending U.S. Patent Publication Nos. 2005/0043598, 2007/0032706, 2007/0016381 and 2008/0033254 describe some algorithms useful in performing data smoothing and/or filtering herein (including signal artifacts replacement), and are incorporated herein by reference in their entirety.

In some embodiments, the receiver electronics module 200 is configured to calibrate the sensor data, and the data storage memory 220 stores the calibrated sensor data points as transformed sensor data. In some further embodiments, the receiver electronics module 200 is configured to wirelessly receive calibration information from a display device, from which the sensor electronics module is configured to calibrate the sensor data. U.S. Pat. Nos. 7,310,544 and 6,931,327 describe some algorithms useful in sensor calibration herein, and are incorporated herein by reference in their entirety.

In some embodiments, the receiver electronics module 200 is configured to perform additional algorithmic processing on the sensor data (e.g., calibrated and/or filtered data and/or other sensor information) and the data storage memory 220 is configured to store the transformed sensor data and/or sensor diagnostic information associated with the algorithms. U.S. Pat. Nos. 7,310,544 and 6,931,327 describe some algorithms that can be processed by the sensor electronics module, and are incorporated herein by reference in their entirety.

Referring again to FIG. 2, receiver electronics module 200 can include a user interface 222 having variety of input/output interfaces, such as one or more buttons 224, a display screen (e.g., an LCD) 226—which can have touch-sensing capabilities—a vibrator 228, an audio transducer (e.g., speaker) 230, backlight, and/or the like. A backlight can be provided, for example, to aid the user in reading the display 226 in low light conditions. The components that comprise the user interface 222 provide controls to interact with the user (e.g., the host). One or more buttons 224 can allow, for example, toggle, menu selection, option selection, status selection, yes/no response to on-screen questions, a "turn off" function (e.g., for an alarm), a "snooze" function (e.g., for an alarm), a reset, and/or the like. The LCD 226 can be provided, for example, to provide the user with visual data output. The audio transducer 230 (e.g., speaker) provides audible signals in response to triggering of certain alerts, such as present and/or predicted hyper- and hypoglycemic conditions. In some embodiments, audible signals are differentiated by tone, volume, duty cycle, pattern, duration, and/or the like. In some embodiments, the audible signal is configured to be silenced (e.g., snoozed or turned off) by pressing one or more buttons 224 on the receiver electronics module 200 and/or by signaling the receiver electronics module using a button or selection on secondary display device 16.

The vibrator 228 can include a motor that provides, for example, tactile signals or alerts for reasons such as described with reference to the audio transducer, above. In one embodiment, the vibrator motor 228 provides a signal in response to triggering of one or more alerts, which can be triggered by the processor module 214 that processes algorithms useful in determining whether alert conditions associated with one or more alerts have been met, for example, present and/or predicted hyper- and hypoglycemic conditions. In some embodiments, one or more different alerts are differentiated by intensity, quantity, pattern, duration, and/or the like. In some embodiments, the alarm is configured to be silenced (e.g., snoozed or turned off) by pressing one or more buttons 224 on the receiver electronics module 200 and/or by signaling the receiver electronics module 200 using a button or selection on a display device (e.g., key fob, cell phone, and/or the like).

Although audio and vibratory alarms are exemplified in FIG. 2, alternative alarming mechanisms can be used in some embodiments. For example, in one alternative embodiment, a tactile alarm is provided including a poking mechanism (not shown) configured to mechanically "poke" the patient in response to one or more alarm conditions.

In another alternative embodiment, the receiver electronics module 200 is configured to transmit sound waves into the host's body (e.g., abdomen or other body part) that will be felt by the host, thereby allowing the host to be alerted without calling attention to himself and/or thereby allowing a hearing-impaired visually-impaired, and/or tactilely-impaired host to be alerted. In some embodiments, the sound waves can be transmitted into the host's body using the electrodes of the sensor itself. In some embodiments, one or more transcutaneous electrodes (other than the electrodes related to analyte measurement) are provided for transmitting sound waves. In some embodiments, electrodes can be provided in the adhesive patch that holds the sensor/sensor electronics module onto the host's body, which can be used to transmit the sound waves. In some embodiments, different sound waves are used to transmit different alarm conditions to the host. The sound waves could be differentiated by any sound characteristic, such as but not limited to amplitude, frequency, and pattern.

In another alternative embodiment, mild electric shock can be used to transmit one or more alarms to the host. Preferably the level of shock would not be overly uncomfortable to the host; however, the intensity of the level of shock can be configured to increase when a host does not respond to (e.g., snooze or turn off) an alert within an amount of time. In some embodiments, the shock can be delivered to the host's body using the electrodes of the sensor itself. In some embodiments, the sensor system can include one or more additional electrodes configured for delivering the shock to the host (alone or in combination with the electrodes related to analyte measurement). In still another example, the one or more electrodes can be disposed on the host's skin, such as in the adhesive patch, for delivering the shock. Alternatively, one or more additional patches, each including an electrode, can be provided, for delivering the shock. The additional patches can be in wired and/or wireless communication with the sensor electronics module.

A telemetry module 232 can be operably connected to the processor module 214 and can provide the hardware, firmware, and/or software that enable wireless communication between the receiver electronics module 200 and one or more remotely located computing devices, such as one or more of sensor unit 8, secondary display device 16 and PC 20 (FIG. 1), for example. A variety of wireless communication technologies that can be implemented in the telemetry module 232 include radio frequency (RF), infrared (IR), Bluetooth, spread spectrum communication, frequency hopping communication, ZigBee, IEEE 802.11/802.16, wireless (e.g., cellular) telecommunication, paging network communication, magnetic induction, satellite data communication, GPRS, ANT, and/or the like. In one embodiment, the telemetry module comprises an ANT chip (i.e. integrated circuit). In some embodiments, ANT technology is implemented in a combination of the telemetry module 232 and the processor module 214. Further, in some embodiments, the telemetry module can include a cellular chip that enables communication over a cellular network. Telemetry module 232 can also include a Global Positioning Satellite chip to permit tracking of a user, which may be useful to locate a user should the user become unconscious or other wise incapacitated.

A battery 234 can be operatively connected to the processor module 214 (and possibly other components of the receiver electronics module 200) and can provide the necessary power for the receiver electronics module 200. In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries can be used to power the receiver electronics module 200. In yet other embodiments, the receiver electronics module 200 can be powered via an inductive coupling, for example.

A battery charger and/or regulator 236 may be configured to receive energy from an internal and/or external charger. In one embodiment, a battery regulator (or balancer) 236 regulates the recharging process by bleeding off excess charge current to allow all cells or batteries in the receiver electronics module 200 to be fully charged without overcharging other cells or batteries. In some embodiments, the battery 234 (or batteries) is configured to be charged via an inductive and/or wireless charging pad. Further, in some embodiments, the battery 234 can be charged when receiver unit 14 is electrically coupled to the secondary display device 16 via a power supply of the secondary display device. When electrically coupled, the secondary display device 16 can also completely or partially power the receiver unit 14. Additionally, in some embodiments, charging the battery 234 via battery charger/regulator can also charge a battery of the secondary display device 16 when the secondary display device 16 is electrically coupled to the receiver unit 14 via communication port 238, for example. Such a connection can be made via a micro-USB connection. One skilled in the art appreciates a variety of known methods of charging batteries, which can be implemented with the system described herein, including wired (cable/plug) and wireless methods.

One or more communication ports 238A-238N, also referred to as external connector(s), can be provided to allow communication with other devices, for example secondary display device 16 and PC 20. In general, communication ports 238 can enable communication with systems that are separate from, or integral with, the sensor electronics module 8. The communication port 238, for example, may comprise a serial (e.g., universal serial bus or "USB") communication port, that allows for communicating with another computer system (e.g., mobile phone, PC, personal digital assistant or "PDA," server, or the like). In one exemplary embodiment, the receiver electronics module 200 is able to transmit historical data stored in electronics module 200 to a mobile phone, PC or other computing device for retrospective analysis by a patient and/or physician via communication port 238.

The receiver electronics module 200 can execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like, which are described in more detail in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, each of which is incorporated herein by reference in its entirety. Furthermore, the receiver electronics module 200 can be configured to store the transformed sensor data (e.g., values, trend information) and to communicate the displayable sensor information to a plurality of different display devices. In some embodiments, the display devices are "dummy" devices, namely, they are configured to display the displayable sensor information as received from the receiver electronics module 200, without any additional sensor data processing.

In some embodiments, receiver module 200 automatically transmits ("pushes") sensor data to secondary display device 16, 20 using telemetry module 232. In this manner, a parent having secondary display device 16, 20 can remotely monitor a child's glucose levels. Secondary display device 16, 20 can additionally have user configurable alerts to alert a parent of a child's glucose level. The secondary display device 16, 20 can also be used to view a trend graph of a child's glucose level over a period of time and/or a calibration status (e.g., when the child last calibrated the glucose monitoring system 1). The secondary display device 14, 20 can also be used to send messages to a child via the child's receiver unit 14, such messaging including reminders for the child to eat, calibrate, administer insulin and the like.

In some embodiments, receiver unit 14 can communicate with a secondary display device 16 or 20 as a two-way radio transceiver.

In some embodiments, a secondary display device can be in the form of a device that has table-top alarm clock functionality and appearance. This device can also incorporate some or all of the features of receiver electronics module 200. In one embodiment, this device is sized and has an appearance similar to traditional alarm clocks placed on a nightstand in a user's bedroom. The alarm clock-type device can have a larger antenna than smaller, handheld receiver units, for example, so it may be more sensitive to wireless transmission and have a larger range for receiving and sending wireless transmissions. This can be useful to detect transmissions from a sensor module 8 if a user is sleeping on top of the sensor module 8 or walking around a house, for example, where a smaller receiver unit may not pick up such transmissions. The alarm clock-type device may also conveniently have larger speakers than a handheld receiver unit and have an adjustable alarm volume so a user can ensure that the user hears an alarm triggered by an alert initiated by the continuous glucose monitoring system 1 using the alarm clock-type device. The alarm clock-type device can also include a display that displays a current glucose value.

In some embodiments, the alarm clock-type device can include a docking station to which a smaller receiver unit 14 can be docked. While docked, the alarm clock-type device can charge the receiver unit 14 and can initiate audible alarms triggered by an alert using the alarm clock-type device's speakers. In addition, an antenna of the alarm clock-type device can be used by the receiver unit 14 to receive transmissions from the sensor module 8.

In some embodiments, the alarm clock-type device can function as a repeater to extend the transmission range of the sensor electronics 12, wherein a transmission from the sensor electronics 12 is received by the alarm clock-type device and then retransmitted using a stronger transmission, for example, to extend the range of the transmission. A receiver unit 14 or other secondary display device may then receive the retransmitted signal.

In some embodiments, a gateway can be included in the glucose monitoring system 1. The gateway can receive a data packet transmission containing sensor-related data from sensor electronics 12 or receiver 14, for example, in a first data format (e.g., format used with ANT or Bluetooth enabled devices), convert the data packet transmission into a second data format (e.g., format compatible with Wi-Fi enabled devices), and transmit the converted data packet. The converted data packet can be transmitted over the Internet to a remote storage device or remote computing system for further processing, for example, or to a receiver unit 14 over a Wi-Fi network.

Exemplary System Configurations

Figure 3:
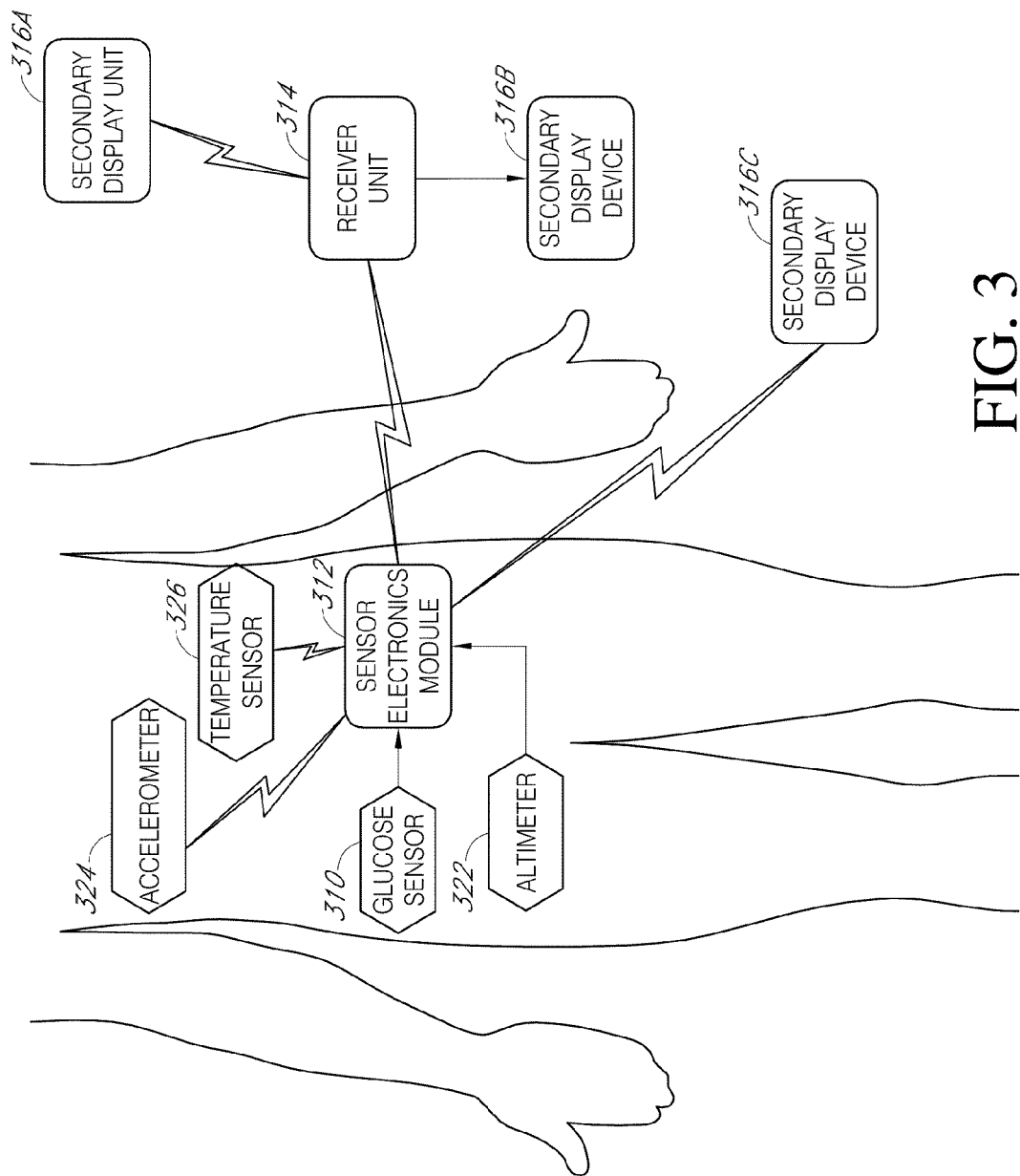
FIG. 3 is a schematic illustrating communication of various components of a glucose monitoring system in accordance with one embodiment of the present invention.

FIG. 3 is a diagram illustrating one embodiment of a receiver unit 314 in communication with sensors electronics module 312 and secondary display units 316A and 316B. Receiver unit 314 can be the same as receiver unit 14, sensor electronics unit 312 can be the same as sensor electronics 12 and secondary display devices 316A-316C can be the same as one or more of secondary display devices 16 and 20. In this embodiment, receiver unit 314 communicates wirelessly directly with sensor electronics unit 312 and secondary display device 316A, and is coupled directly to secondary display device 316B via a mechanical communication port.

Further to FIG. 3, sensor electronics unit 312 is in communication with various sensors, including a glucose sensor 310, altimeter 322, an accelerometer 324, and a temperature sensor 326. In this embodiment, each of the sensors 324 and 326 communicate sensor data wirelessly to the sensor electronics unit 312 and each of sensors 310 and 322 are directly coupled to the sensor electronics unit 312 via one or more electrical communication wires. In other embodiments, the sensor electronics unit 312 incorporates one or more of the sensors 310, 322, 324 and 326. In other embodiments, one or more of the sensors 310, 322, 324 and 326 are combined as a single sensor unit, such as a combined glucose/temperature sensor that transmits sensor data to the sensor electronics unit 312 using common communication circuitry. Depending on the embodiment, fewer or additional sensors may communicate with the sensor electronics unit 312. In other embodiments, one or more of the sensors 320-328 is directly coupled to the sensor electronics unit 312, such as via one or more electrical communication wires.

In addition to receiver unit 314, sensor electronics unit 312 communicates wirelessly with secondary display unit 316C. The sensor electronics unit 312 can generate and transmit data packages to receiver unit 314 and display device 316C, each of which can be configured to receive, store, retransmit, and/or display displayable sensor data. In some embodiments, the sensor electronics unit 312 analyzes the sensor data from the multiple sensors and determines which displayable sensor data is to be transmitted to the particular receiver unit 314 or display device 316C, based on one or more of many characteristics of the host, the receiver unit 314, the display device 316C, a user of the display device 316C, and characteristics of the sensor data and/or the transformed sensor data. Thus, customized displayable sensor information can be transmitted to the receiver unit 314 and/or display device 316C and each device can display the sensor information with minimal processing by the respective receiver unit 314 and display device 316C.

In the embodiment of FIG. 3, the various components communicate wirelessly with one another via Bluetooth or ANT communication protocols, for example.

FIG. 3 also illustrates the sensor electronics unit 312 indirectly communicating with secondary display devices 316A and 316B. In other words, data is directly transmitted to receiver unit 314, which then transmits sensor data to secondary display devices 316A and 316B.

Figure 4:
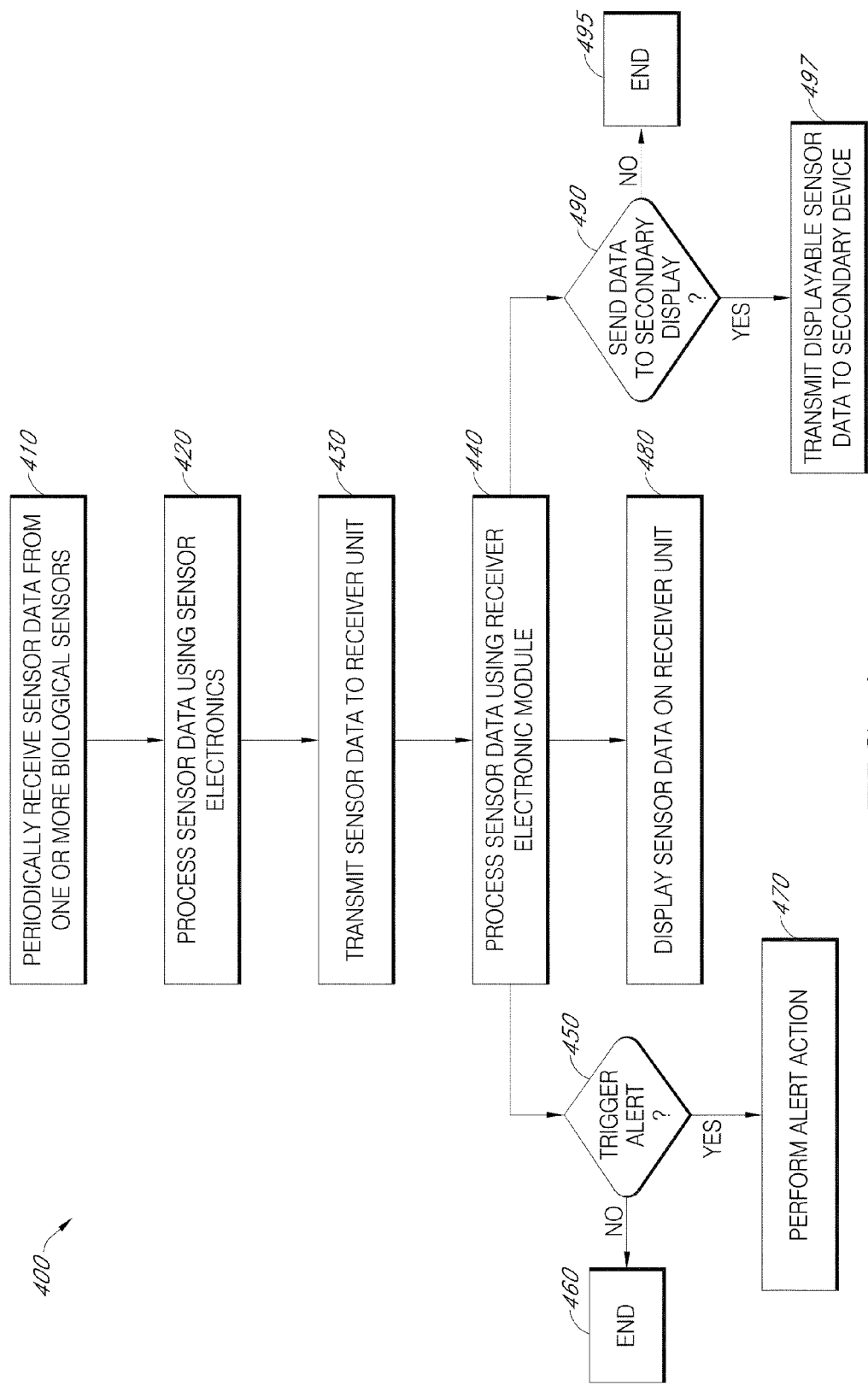
FIG. 4 is flowchart depicting a process of using a receiver unit as a stand alone device and in combination with a secondary display device in accordance with one embodiment of the present invention.

FIG. 4 is a flowchart illustrating one embodiment of a method 400 of using a receiver unit, such as receiver unit 14 or 314, first as a stand alone device and then used in combination with a secondary display device, such as secondary device 16, 20, 316A, 316B or 316C. As noted above, embodiments of the receiver unit discussed herein can be used as a stand alone medical device as well as a combination with another device to enhance processing and displaying functionality. The various tasks performed in connection with process 400 may be performed by hardware, software, firmware, or any combination thereof. It should be appreciated that process 400 may include any number of additional or alternative tasks. The tasks shown in FIG. 4 need not be performed in the illustrated order and process 400 may be incorporated into a more comprehensive procedure or process having additional functionality not described in detail herein.

Beginning in block 410, the sensor electronics unit 12, 312 intermittently receives and/or processes sensor data from one or more sensors, such as a glucose sensor, accelerometer, altimeter, or any other sensor described herein. Each sensor that transmits sensor data to the sensor electronics unit 12, 312 may have a predetermined or dynamic schedule for transmitting sensor data. For example, a first sensor may transmit sensor data to the sensor electronics unit 12, 312 on a consistent periodic basis, such as one sensor data point per minute, 5 minutes, 10 minutes, 30 minutes etc., while a second sensor may transmit sensor data to the sensor electronics unit 12, 312 only when the sensor data reaches a certain threshold. For example, an altimeter may only transmit sensor data to the sensor electronics module when an altitude of the altimeter is above a predetermined threshold.

Moving to block 420, the sensor data received from the one or more sensors is stored, such as in one or more memories and/or storage devices of the sensor electronics unit 12, 312 and optionally processed by the sensor electronics unit 12, 312.

Next, in block 430 the sensor electronics unit 12, 312 transmits the sensor data to the receiver unit 14, 314. As discussed above, the sensor data that is transmitted to the receiver unit 14, 314 can be raw sensor data, slightly processed sensor data (e.g., merely smoothed using a smoothing filter) or the sensor data can be processed so that it is displayable sensor data.

In block 440, the receiver unit 14, 314 processes the sensor data received from the sensor electronics unit 12, 312. The processing performed by the receiver unit 14, 314 can include any of the processing described herein.

Next, the process 400 can split into three different branches. Each of the branches can be performed in parallel or sequentially.

A first branch proceeds to decision block 450, which decides whether to trigger an alert. As noted above, each alert can be associated with one or more alert conditions that must be met in order for the respective alert to trigger. The alert conditions could be any characteristic of the sensor data, transformed sensor data, a display device, a host, or an operator of a display device, along with other characteristics. For example, two different alerts that are each related to the host reaching a hypoglycemic glucose level may have slightly different alert conditions that must be satisfied in order to trigger the alerts. For example, a first hypoglycemic alert may require that the host's glucose level is below a first threshold and that a temperature of the host is above a certain threshold, while a second hypoglycemic alert may only require that the host's glucose level is below a second threshold (which may be slightly lower than the first threshold). In this embodiment, the first and second hypoglycemic alerts may be associated with actions that are quite different, such as transmission of data packages of various contents and formatting to different display devices. If it is determined that an alert is not triggered, then the first branch ends and block 460. As discussed above, alerts may be triggered based on raw sensor data, transformed sensor data (e.g., calibrated and/or filtered data), or any other data from one or more sensors.

If the receiver unit 14 determines that an alert has triggered in block 450, the method continues to block 470 where one or more actions associated with the triggered alert are initiated. An action can include alarms that are associated with the receiver electronics module 200 discussed above, such as activation of a vibrator motor or audio transducer, for example.

In the second branch of process 400, the receiver unit 14, 314 displays sensor data on the receiver unit based on the processed sensor data in block 440.

In the third branch of the process 400, the receiver unit 14, 314 determines whether to send data to a secondary display device, such as secondary display device 16, 20, 316A, 316B or 316C. This decision can be based on whether a secondary device is communicatively coupled to the receiver unit 14, 314 and/or whether the secondary device is ready to receive sensor data. For example, the secondary device may be communicatively coupled to the receiver unit but be placed in a sleep mode or otherwise configured not ready to receive sensor data from the receiver unit. Should the receiver unit 14, 314 determine not to send sensor data to a secondary display device, then the third branch of process ends at block 495.

However, if the receiver unit 14, 314 determines to send sensor data to a secondary display device in decision block 490, then the receiver unit can transmit displayable sensor data to the secondary display device in block 497. The secondary display device can then use the displayable sensor data to generate reports based on the sensor data and display the reports of a display of the secondary device, for example. In one embodiment, the displayable device stores the sensor data and can additionally prepare retrospective reports based on received sensor data. In addition, a user can input other information into the secondary device upon which reports can be generated, including information indicative of when a particular action was taken by the host, such as when carbohydrates were consumed, when insulin was taken, when exercise was performed, when any relevant change in the health of the host occurs, and/or any other event that might possible effect the sensor data.

Figure 5:
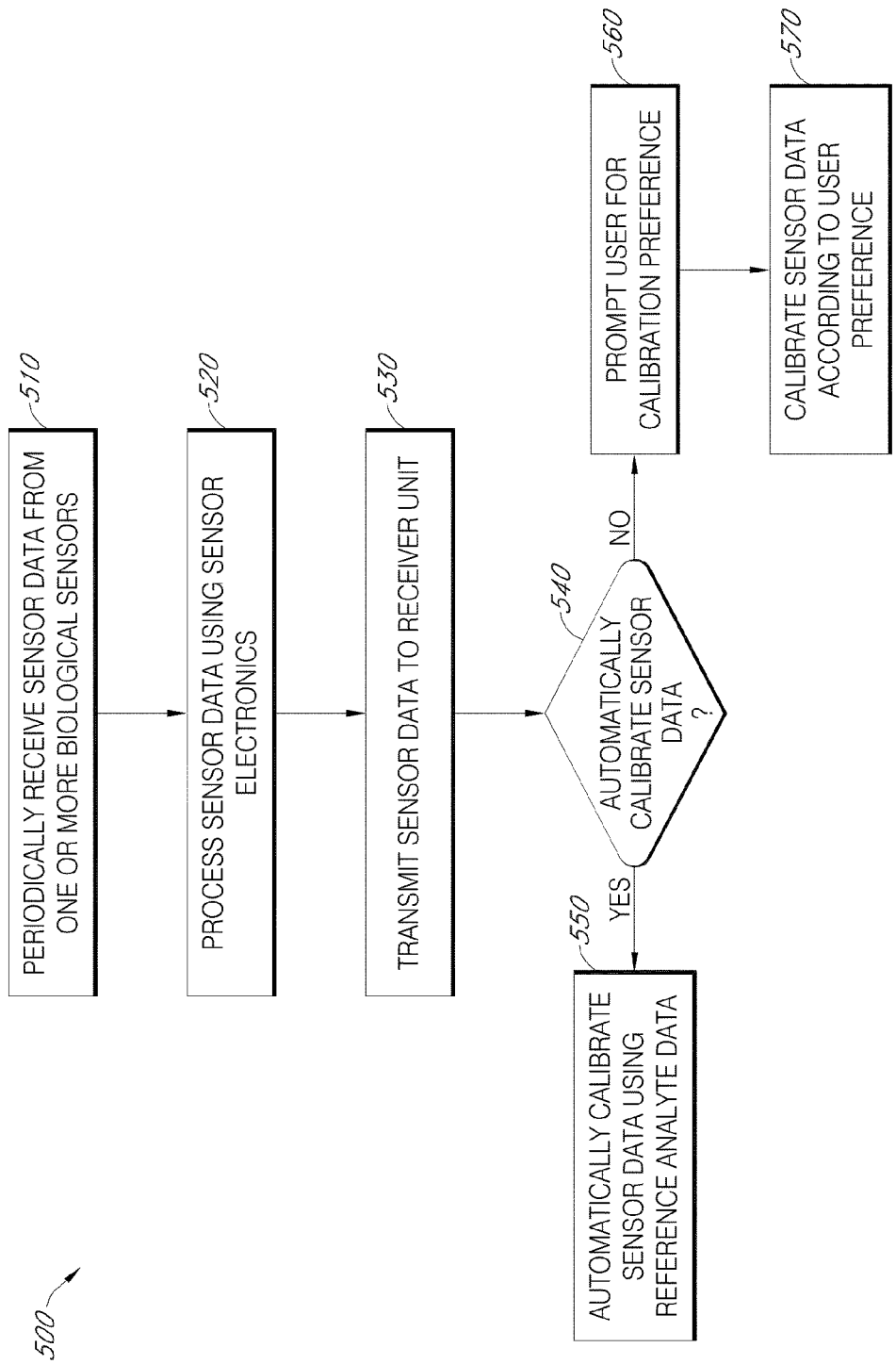
FIG. 5 is a flowchart depicting a process of calibrating sensor data in accordance with one embodiment of the present invention.

FIG. 5 is a flowchart illustrating one embodiment of a calibration method 500 using a receiver unit 14, 314. As noted above, embodiments of the receiver unit 14, 314 discussed herein can be used as a stand alone medical device as well as a combination with secondary display device to enhance processing and displaying functionality. According to method 500, calibration of sensor data can occur automatically when the receiver unit 14, 314 is not communicatively and/or physically coupled to a secondary display device 16, 20, 316A, 316B or 316C (e.g., is operating as a standalone device) and calibration can optionally occur with manual entry of a calibration value when the receiver unit is connected to the secondary device. The various tasks performed in connection with process 500 may be performed by hardware, software, firmware, or any combination thereof. It should be appreciated that process 500 may include any number of additional or alternative tasks. The tasks shown in FIG. 5 need not be performed in the illustrated order and process 500 may be incorporated into a more comprehensive procedure or process having additional functionality not described in detail herein.

Beginning in block 510, the sensor electronics unit 12, 312 intermittently receives and/or processes sensor data from one or more sensors, such as a glucose sensor, accelerometer, altimeter, or any other sensor described herein.

Moving to block 520, the sensor data received from the one or more sensors is stored, such as in one or more memories and/or storage devices of the sensor electronics unit 12, 312 and optionally processed by the sensor electronics unit.

Next, in block 530 the sensor electronics unit 21, 312 transmits the sensor data to the receiver unit 14, 314. As discussed above, the sensor data that is transmitted to the receiver unit 14, 314 can be raw sensor data, slightly processed sensor data (e.g., merely smoothed using a smoothing filter) or the sensor data can be processed so that it is displayable sensor data.

In decision block 540, the receiver unit 14, 314 decides whether to automatically calibrate the sensor data using reference analyte data or allow user input in the calibration process. In one embodiment, the receiver unit 14, 314 determines whether or not the receiver unit is connected to a secondary display device, and if the receiver unit is not connected, then the process 500 proceeds to block 550. If it is determined that the receiver unit 14, 314 is connected to a secondary display device, then process 500 proceeds to block 560.

In block 550, the receiver unit 14, 314 automatically calibrates the sensor data using reference analyte data obtained from a reference analyte meter. As noted above, the reference analyte meter can be integral with the receiver unit 14, 314.

In contrast, in block 560, the receiver unit 14, 314 communicates with the display device to prompt the user for input related to calibrating the sensor data. The input can be received via a user interface of the secondary display device and the input can be indicative of a user selection related to use reference data. For example, the user input can be indicative of a user preference to calibrate the sensor data using the most current reference data, ignore the most current reference data and/or a manual entry of current calibration data. The receiver unit 14, 314 can then calibrate the sensor data based on the received user input preference(s).

Next, in block 570, the sensor data is calibrated according to the user preferences inputted in block 560.

Figure 6:
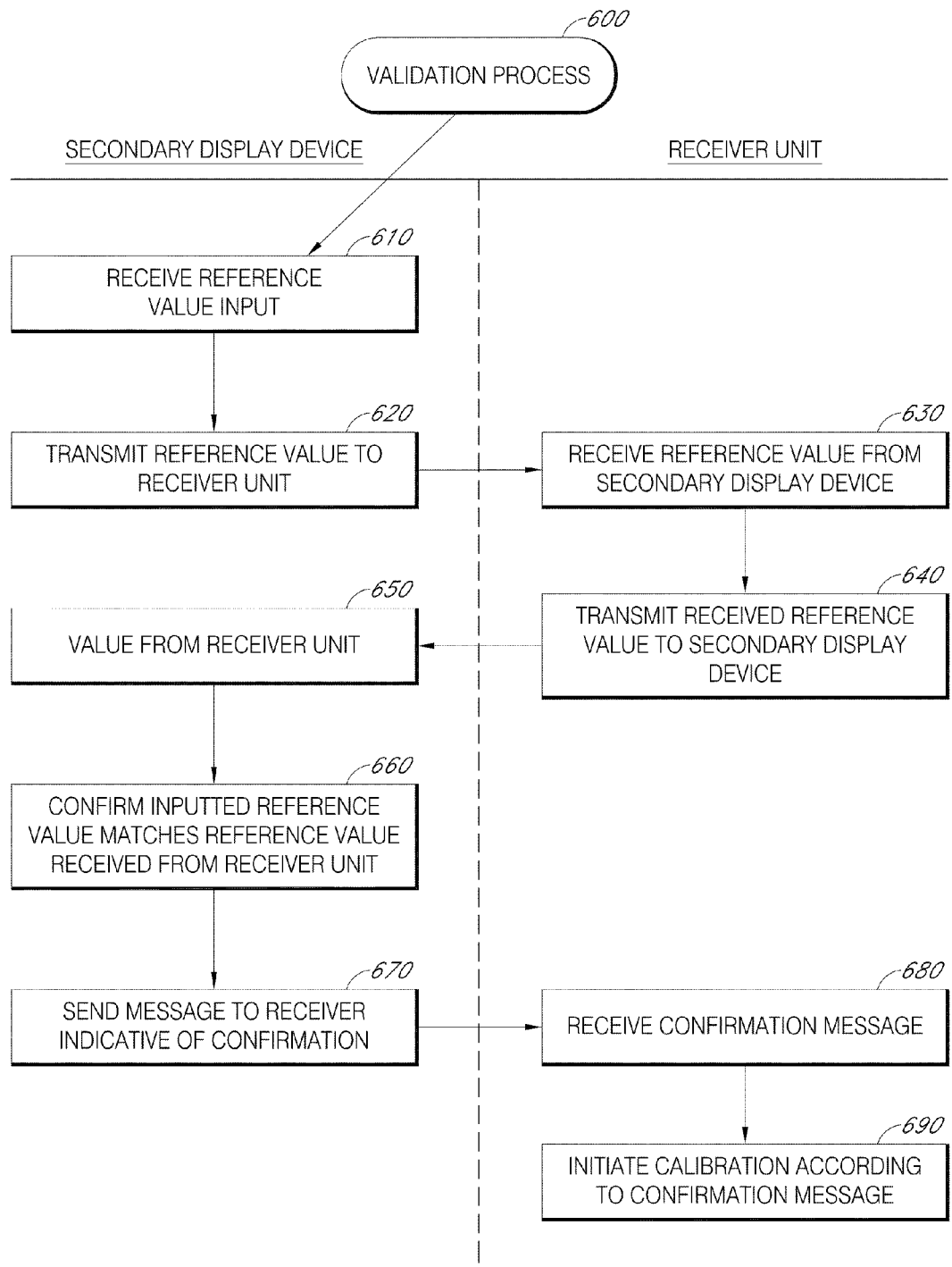
FIG. 6 is a flow chart depicting a process for validating a manually inputted reference data value in accordance with one embodiment of the present invention.

In one embodiment, a reference data value is validated if the reference value is manually inputted using a secondary display device 16, 20, 316A, 316B or 316C in block 560. The following validation process 600 is a non-limiting example of one way in which a reference data value can be validated after the reference value is inputted in step 560. It is noted that the below process is described in terms of validating a reference value using secondary display device 16 and receiver unit 14, but it is appreciated the validation process 600 can also be used between any two computing devices of the monitoring system 1, such as directly between secondary display device 16 or 20 and sensor module 8 of FIG. 1. The various tasks performed in connection with process 600 may be performed by hardware, software, firmware, or any combination thereof. It should be appreciated that process 600 may include any number of additional or alternative tasks. The tasks shown in FIG. 6 need not be performed in the illustrated order and process 600 may be incorporated into a more comprehensive procedure or process having additional functionality not described in detail herein.

First, process 600 can begin with receipt of an inputted reference value in the manner described above in block 560 of FIG. 5. The reference data value can be stored in memory of the secondary display device and transmitted from the secondary device 16, 20, 316A, 316B or 316C to the receiver unit 14, 314 (in a data packet, for example) via respective communication ports of the devices at block 610. At block 640, the receiver unit 14, 314 transmits a message back to the secondary display device containing the reference value it received at block 630. Receiver unit can also optionally concurrently or sequentially display the reference value on a display of the receiver unit at block 640 so to provide a user an indication that the reference value was received by the receiver device and/or confirm that the value of the reference value is the correct reference value.

Next, the secondary display device receives the reference value transmitted from the receiver unit at block 650 and confirms the reference value received from the receiver unit is the same as the reference value inputted and stored on the secondary display device at block 660. Confirming the reference value can include electronically comparing (using a processor of the secondary display device, for example) the reference value inputted into the secondary display device at block 610 to the reference value received from the receiver unit 14, 314 at block 650 to confirm that the values match. Additionally or alternatively, the secondary display device can display the confirmed reference value on the display of the secondary device and prompt the user to confirm the reference value using the secondary display device's user interface. The reference value can be considered valid once the secondary device confirms the values match based upon the electronic matching and/or user input confirmation responsive to the user prompt.

At block 670, the secondary display device can send a message to the receiver unit 14, 314 indicative of the reference value being confirmed (i.e. valid). The receiver unit 14, 314 can receive the confirmation message at block 680 and then proceed to calibrating sensor data at block 690 according to the confirmation message, such as initiating calibration using the reference value if the confirmation message indicates that the reference value is valid. If the confirmation message indicates that the reference value is not valid, then calibrating the sensor data using the reference value can be suspended.

In accordance with some embodiments, if any of the above steps are not completed in process 600, then the reference value is not used and the secondary display device prompts the user to re-enter a reference value and thereafter repeat the above validation process 600 using the re-entered reference value.

Exemplary User Interface

An embodiment of a user interface 700 of a display device, such as display device 16, 20, 316A, 316B or 316C, will now be discussed with reference to FIGS. 7A-7E. As illustrated, user interface 700 of display device can provide an interface for a user to view sensor related data, to input data and to modify settings, among other things. In some embodiments, the user interface includes a user interface software module can be stored in memory of the display device and can include instructions, when executed by a processor of the display device, for displaying user interface and receiving and processing data for operating user interface and any other actions described herein. The software program embodying the software module can be, for example, an application downloaded from a remote server via the Internet or some other network communication medium.

In one embodiment, the display device is an Apple iPhone and the software program is an application downloaded via Apple's iTunes internet site. Alternatively, the software program can be downloaded from a computer, such as a physician's computer, or transmitted from another mobile communication device. A user selectable icon associated with the application can be displayed on the display device and the display device can automatically launch the application upon user selection of the selectable icon. The application can also run in the background of the display device and provide alerts to the user upon the occurrence of an event.

In one embodiment, the user selectable icon displayed on the display device includes a current glucose concentration value determined by the monitoring system 1. The current glucose concentration value of the icon can be updated each time a new glucose concentration value is provided using the monitoring system 1. In this manner, a user need not open the application to view the current glucose value, but rather view the current glucose value associated with the icon of the application. Should the user want to perform an additional action associated with the glucose monitoring system 1, then the user can launch the interface 700 by selecting the icon associated with the application, for example.

Figure 7B:
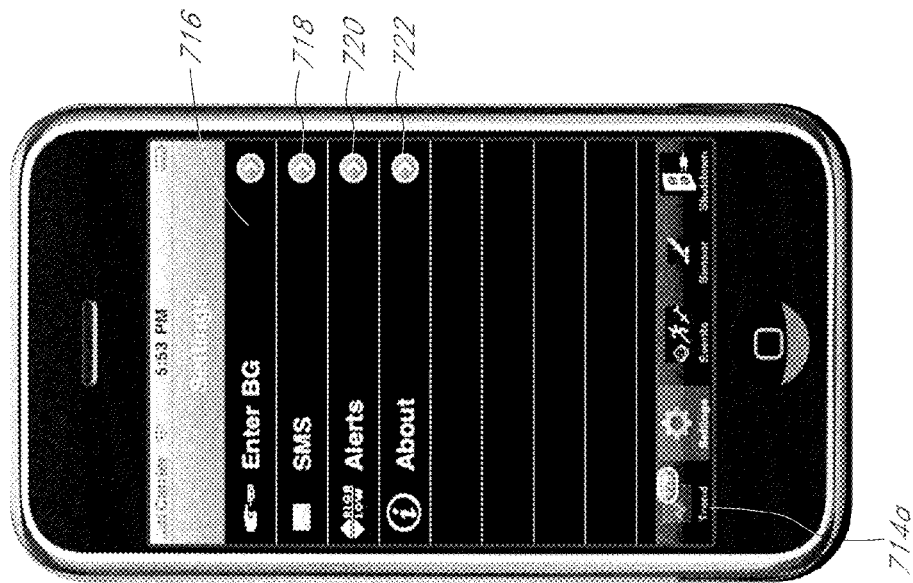
FIGS. 7A-7E illustrate exemplary user interface display screens of a user interface of a glucose monitoring system in accordance with one embodiment.
Figure 7A:
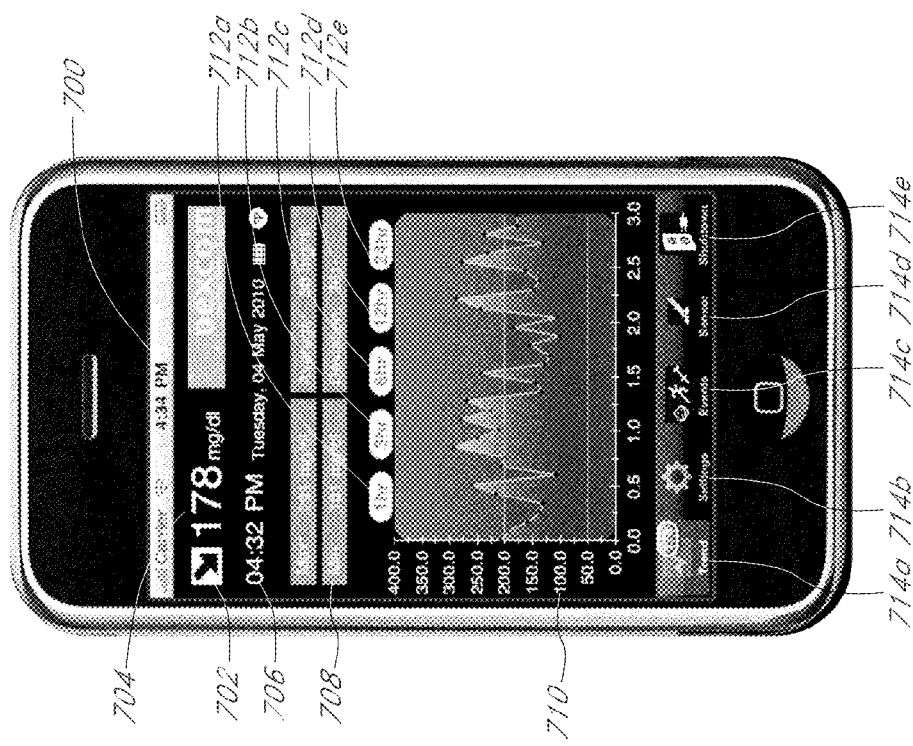

FIG. 7A illustrates a first screen of the user interface 700 in accordance with one embodiment. The first screen displays a variety of sensor data related information including, but not limited to, a trend arrow 702, a most current glucose concentration value 704, date and time of the most recent sensor data update 706 (e.g., date and time when last received data directly or indirectly from sensor electronics unit 12, 312), maximum, minimum, deviation and average glucose values during a predetermined time period 708, and a graph displaying past glucose values measured over a predetermined time period (a "trend graph") 710. Note that the user interface 700 also includes user selectable icons 712a-712e that can be selected by touching the icons on the display of the display device corresponding to various time periods. By selecting one of the time periods, the user interface can retrospectively analyze the glucose data that falls within the selected time period and display the analysis on the user interface. The time periods displayed in the embodiment of FIG. 7A include 1, 3, 6, 12 and 24 hour time periods, but other time periods can be used as appreciated by one of skill in the art.

As illustrated in FIG. 7A, the user interface 700 can also include a row of different user selectable icons 714a -714e corresponding to different views and/or functions of the user interface 700. For example, selecting one of the icons 714 can switch the user interface 700 to a display screen corresponding to that icon. For example, selecting the "trend" icon 714a in the row of icons displays a trend view like that of FIG. 7A, and selecting the "settings" icon 714b can switch the user interface to a settings screen, such as the one illustrated in FIG. 7B. In addition, selecting the "events" icon 714c can cause the user interface 700 to display a screen that allows a user to view and/or input information related an event using the user interface. Such event related information that can be viewed and/or inputted can include exercise related information (e.g., exercise activity type, time of start and finish of exercise, amount of calories burned during exercise), meal related information (e.g., time a meal was consumed and caloric content of the meal) and medication dosage related information (e.g., insulin administration time and amount, and insulin type that was administered). Selecting the "sensor" icon 714d can cause the user interface 700 to display a screen, such as a display screen illustrated in FIG. 7D, which allows a user to selectively initiate functions or input information related to a sensor, such as sensor 10 of the glucose monitoring system 1 discussed in FIG. 1. In addition, the icons 714 can be associated with a function, such as shutting down the sensor monitoring system 1 associated with the icon 714e. Pressing icon 714e. can cause the user interface to display a screen allowing a user to selectively power down fully or partially one or more of an application running the user interface 700, a receiver unit 14, 314 of the sensor system and sensor electronics unit 12, 312. Alternatively, selecting the "shutdown" icon 716e can automatically shutdown one or more of the above described elements of the glucose monitoring system 1 without requiring further user input.

Note that a bubble icon can also be displayed over one of the icons 714a-714e to provide additional information to the icon 714a-714e. For example, FIGS. 7A-7D each illustrate a bubble icon containing a numerical value of over the "trend" icon 714a. This numerical value can corresponds to the most currently known measured glucose value. Displaying information in this manner can conveniently provide the user with important information regardless of the screen the user interface 700 is currently displaying.

Further to FIG. 7B, the user interface 700 can include a settings screen that allows a user to select and modify settings of a glucose monitoring system. These settings can be related to settings of the glucose monitoring system 1, such as a receiver unit 14, secondary display device 16, 20, sensor electronics module 8, or other devices associated with the monitoring system like an insulin pump. In the exemplary settings screen of FIG. 7B, the user interface 700 can include a menu of a plurality of selectable items. Functions associated with the plurality of selectable items include: inputting a blood glucose (BG) reference value for use with calibrating continuous glucose sensor data 716, for example; modifying settings relating to sending SMS alerts 718; modifying high and low blood glucose threshold alerts 720; and an "about" setting 722 that can initiate a "help" process that allows a user to query for information related to the glucose monitoring system 1.

Figure 7C:
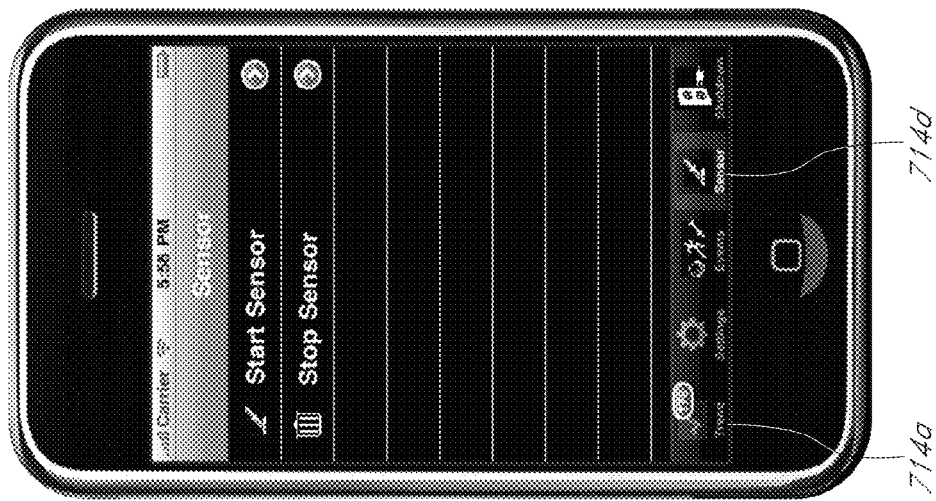

FIG. 7C illustrates a manual blood glucose reference value input screen. This screen can be displayed on user interface 700 in response to a user selecting the "Enter BG" item 716 on the settings screen of FIG. 7B. Here, a user can input a reference blood glucose value obtained from a glucose meter, for example.

Figure 7D:
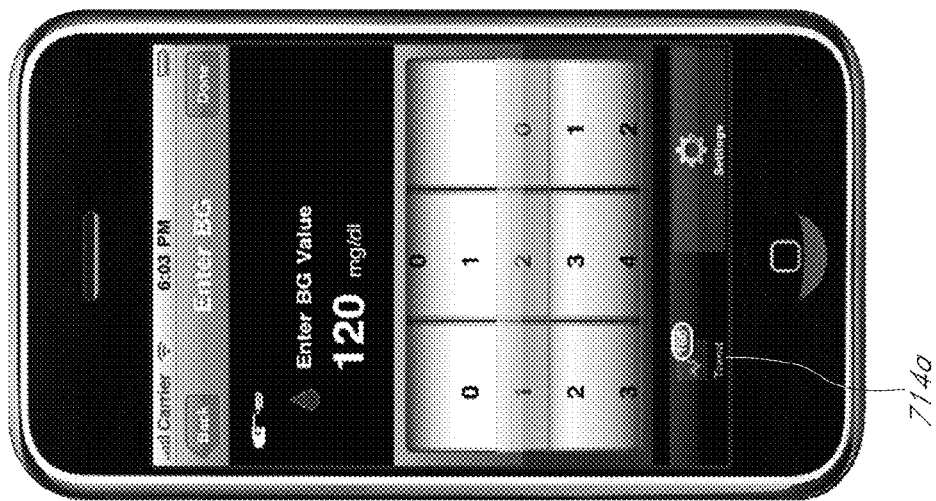

FIG. 7D is a sensor screen that can be displayed if a user selects the sensor icon 714d as discussed above. Here, a user can selectively start and stop operation of a glucose sensor, such as sensor 10 of FIG. 1. In some embodiments, starting and stopping the sensor can be accomplished by powering down or powering up, respectively, circuitry of the sensor electronics unit 12 that drives the sensor 8.

Figure 7E:
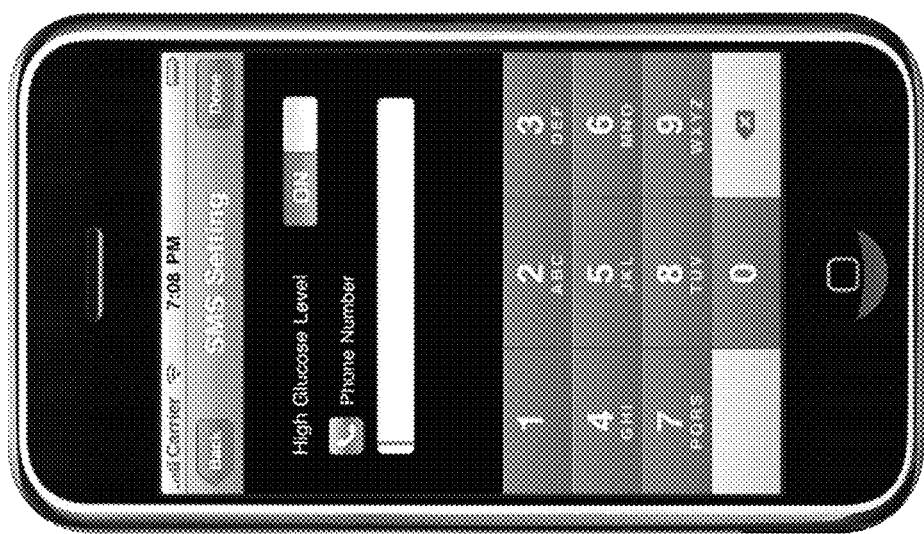

FIG. 7E illustrates a short message service "SMS" settings screen that the user interface 700 can display in response to a user selection of the "SMS" item in the settings screen of FIG. 7B. Here, the user interface 700 can be used by a user to modifying settings relating to sending SMS alerts, such as when to will automatically send an SMS alert to one or more remote devices or computing systems upon an occurrence of an event (e.g., when a high or low glucose threshold is exceeded) and inputting phone number(s) to which the SMS alert is to be sent upon the occurrence of the associated event. As an example, an SMS including information related to the alert can be automatically sent to a device associated with parent, physician, and/or local emergency service. Although FIG. 7E relates to sending SMS alerts, embodiments can send alerts using other communication vehicles in addition to or in place of SMS, such as email, voice telephone calls and the like.

User interface 700 can also include other features, such as a display screen which prompts a user to order more sensors or other supplies. In one example, a computing system can track a number of remaining, unused sensors that a user has and automatically prompt, via the user interface 700, the user to order more sensors when the number of remaining sensors is less than a threshold amount. The user interface can also initiate an order of additional supplies, such as additional sensors, upon receiving user input indicative of the order.

The user interface 700 can also display a user selectable item, that when selected, provides a geographic location of a receiver unit, such as receiver unit 14, of the glucose monitoring system 1. This way, a user can locate a lost receiver unit or a parent can locate a child having the receiver unit, for example.

In some embodiments, the user interface 700 can display a user selectable item that initiates a process for uploading sensor data related information to remote computing device. In one example, a user can select the user selectable item to initiate a process to interface the glucose monitoring system 1 with a social media Internet web site and allow the user to upload selected sensor data related information to the social media Internet web site. Once interfaced with the social media Internet web site, the user interface 700 can also be used by a user to connect with other people that may have similar problems encountered by the user or to search for information related to a problem encountered by the user.

In some embodiments, the user interface 700 can display a user selectable item that when selected automatically connects the user via a communication medium (e.g., Internet, cellular network) to customer support associated with the glucose monitoring system 1. Once connected, the user can communicate using the user interface with the customer support to resolve an issue, for example.

In some embodiments, user interface 700 can be used to connect a user with a remotely located communication device. In the following non-limiting example, the user communicates with a clinician using the interface 700, although it is appreciated the user can communicate with any person using the interface. The user interface 700 can include a selectable remote consultation item, that when selected, causes the user interface to connect with a device of the clinician, which may have a similar user interface as user interface 700. The connection can be over any communication medium such as the Internet or cellular network. Once communication is established, a user can communicate using video (user interface 700 can include a video camera) and/or voice with the remotely located device. In this manner, a user can conduct a remote consultation with their clinician.

In some embodiments, the user interface 700 automatically sends data, such as sensor data, to the clinician's device. The transmission can occur at periodic intervals (e.g., weekly) or after a pattern or clinical condition has been detected (e.g., two consecutive nights of hypoglycemia longer than 60 minutes) and the sensor data can include any amount of historical sensor data, such as the past week or months worth of sensor data. Alternatively, the sensor data sent to the clinician's device need only be the sensor data determined to relate to the pattern of clinical condition that was detected that triggered the transmission.

A remote consultation meeting can also be set up automatically with the user based on a predetermined prioritization of a clinical urgency associated with the detected pattern or clinical condition. As an example, if a clinical condition is determined, then the user interface 700 can initiate a computer-implemented process that sets a day and time for an appointment with the user and the clinician. The time and date can be selected based upon previously arranged appointments by the clinician and the user, and a priority associated a clinical urgency of the detected clinical condition. The appointment time and day can be automatically stored in the user interface and user interface 700 can automatically output reminders to the user using user interface 700, such as displaying messages or sounding audible alarms, to remind the user of the scheduled appointment. The user can then initiate a remote consultation with the clinician at the scheduled time and day by selecting the selectable remote consultation item on the user interface 700.

While in the remote consultation, the user and clinician can also bring up sensor data to review on the user interface 700. For example, the user interface 700 can be used to select sensor data and transmit the selected data to the clinician for display on the clinician's device other otherwise indicate the selected sensor data so that the clinician's device displays the selected data on the clinician's device. In other words, user interface 700 can cause a shared view of selected sensor data on both the user's device and the clinician's device. Either the user or the clinician can also control the shared view to scroll through a time series of the data, zoom in or out on select windows of the data, view summary charts of clinical outcomes (e.g., time spent in different glucose zones), and troubleshoot problems.

The user interface 700 can also allow in-silico testing of suggested behavior modifications (e.g., change to programmed carbohydrate ratio, timing of insulin injections and the like), and for the suggested modifications to be simulated on the historical sensor data stored on the system 1. The in-silico testing can be performed using a shared view using user interface 700 while in a remote consultation with the clinician, or can be performed solely using the user interface 700.

The user interface 700 can also include software that stores and tracks a clinician's diagnosis and/or recommendations for subsequent review by the user and for historical review by the clinician. In some embodiments, the clinician inputs a diagnosis and/or recommendation using the physician's computing device while in the remote consultation or after the remote consultation. The inputs a diagnosis and/or recommendation can be transmitted to the user interface 700 and stored in memory of the computing device that incorporates the user interface 700 for later tracking and review.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; U.S. Publ. No. US-2003-0032874-A1; U.S. Publ. No. US-2005-0027180-A1; U.S. Publ. No. US-2005-0033132-A1; U.S. Publ. No. US-2005-0043598-A1; U.S. Publ. No. US-2005-0051427-A1; U.S. Publ. No. US-2005-0090607-A1; U.S. Publ. No. US-2005-0176136-A1; U.S. Publ. No. US-2005-0203360-A1; U.S. Publ. No. US-2005-0242479-A1; U.S. Publ. No. US-2005-0245799-A1; U.S. Publ. No. US-2006-0015020-A1; U.S. Publ. No. US-2006-0016700-A1; U.S. Publ. No. US-2006-0020188-A1; U.S. Publ. No. US-2006-0020190-A1; U.S. Publ. No. US-2006-0020191-A1; U.S. Publ. No. US-2006-0020192-A1; U.S. Publ. No. US-2006-0036140-A1; U.S. Publ. No. US-2006-0036141-A1; U.S. Publ. No. US-2006-0036143-A1; U.S. Publ. No. US-2006-0040402-A1; U.S. Publ. No. US-2006-0068208-A1; U.S. Publ. No. US-2006-0086624-A1; U.S. Publ. No. US-2006-0142651-A1; U.S. Publ. No. US-2006-0155180-A1; U.S. Publ. No. US-2006-0189856-A1; U.S. Publ. No. US-2006-0198864-A1; U.S. Publ. No. US-2006-0200019-A1; U.S. Publ. No. US-2006-0200020-A1; U.S. Publ. No. US-2006-0200022-A1; U.S. Publ. No. US-2006-0200970-A1; U.S. Publ. No. US-2006-0204536-A1; U.S. Publ. No. US-2006-0224108-A1; U.S. Publ. No. US-2006-0235285-A1; U.S. Publ. No. US-2006-0249381-A1; U.S. Publ. No. US-2006-0252027-A1; U.S. Publ. No. US-2006-0253012-A1; U.S. Publ. No. US-2006-0257995-A1; U.S. Publ. No. US-2006-0257996-A1; U.S. Publ. No. US-2006-0258761-A1; U.S. Publ. No. US-2006-0263763-A1; U.S. Publ. No. US-2006-0270922-A1; U.S. Publ. No. US-2006-0270923-A1; U.S. Publ. No. US-2007-0016381-A1; U.S. Publ. No. US-2007-0027370-A1; U.S. Publ. No. US-2007-0032706-A1; U.S. Publ. No. US-2007-0032718-A1; U.S. Publ. No. US-2007-0045902-A1; U.S. Publ. No. US-2007-0059196-A1; U.S. Publ. No. US-2007-0066873-A1; U.S. Publ. No. US-2007-0163880-A1; U.S. Publ. No. US-2007-0173708 A9; U.S. Publ. No. US-2007-0173709-A1; U.S. Publ. No. US-2007-0173710-A1; U.S. Publ. No. US-2007-0197889-A1; U.S. Publ. No. US-2007-0203966-A1; U.S. Publ. No. US-2007-0208244-A1; U.S. Publ. No. US-2007-0208245-A1; U.S. Publ. No. US-2007-0208246-A1; U.S. Publ. No. US-2007-0232879-A1; U.S. Publ. No. US-2007-0235331-A1; U.S. Publ. No. US-2008-0021666-A1; U.S. Publ. No. US-2008-0033254-A1; U.S. Publ. No. US-2008-0045824-A1; U.S. Publ. No. US-2008-0071156-A1; U.S. Publ. No. US-2008-0083617-A1; U.S. Publ. No. US-2008-0086044-A1; U.S. Publ. No. US-2008-0119703-A1; U.S. Publ. No. US-2008-0119704-A1; U.S. Publ. No. US-2008-0119706-A1; U.S. Publ. No. US-2008-0183061-A1; U.S. Publ. No. US-2008-0183399-A1; U.S. Publ. No. US-2008-0188731-A1; U.S. Publ. No. US-2008-0189051-A1; U.S. Publ. No. US-2008-0194938-A1; U.S. Publ. No. US-2008-0197024-A1; U.S. Publ. No. US-2008-0200788-A1; U.S. Publ. No. US-2008-0200789-A1; U.S. Publ. No. US-2008-0200791-A1; U.S. Publ. No. US-2008-0214915-A1; U.S. Publ. No. US-2008-0228054-A1; U.S. Publ. No. US-2008-0242961-A1; U.S. Publ. No. US-2008-0262469-A1; U.S. Publ. No. US-2008-0275313-A1; U.S. Publ. No. US-2008-0287764-A1; U.S. Publ. No. US-2008-0287765-A1; U.S. Publ. No. US-2008-0306368-A1; U.S. Publ. No. US-2008-0306434-A1; U.S. Publ. No. US-2008-0306435-A1; U.S. Publ. No. US-2008-0306444-A1; U.S. Publ. No. US-2009-0012379-A1; U.S. Publ. No. US-2009-0018424-A1; U.S. Publ. No. US-2009-0030294-A1; U.S. Publ. No. US-2009-0036758-A1; U.S. Publ. No. US-2009-0036763-A1; U.S. Publ. No. US-2009-0043181-A1; U.S. Publ. No. US-2009-0043182-A1; U.S. Publ. No. US-2009-0043525-A1; U.S. Publ. No. US-2009-0043541-A1; U.S. Publ. No. US-2009-0043542-A1; U.S. Publ. No. US-2009-0045055-A1; U.S. Publ. No. US-2009-0062633-A1; U.S. Publ. No. US-2009-0062635-A1; U.S. Publ. No. US-2009-0076360-A1; U.S. Publ. No. US-2009-0076361-A1; U.S. Publ. No. US-2009-0099436-A1; U.S. Publ. No. US-2009-0124877-A1; U.S. Publ. No. US-2009-0124879-A1; U.S. Publ. No. US-2009-0124964-A1; U.S. Publ. No. US-2009-0131768-A1; U.S. Publ. No. US-2009-0131769-A1; U.S. Publ. No. US-2009-0131776-A1; U.S. Publ. No. US-2009-0131777-A1; U.S. Publ. No. US-2009-0137886-A1; U.S. Publ. No. US-2009-0137887-A1; U.S. Publ. No. US-2009-0143659-A1; U.S. Publ. No. US-2009-0143660-A1; U.S. Publ. No. US-2009-0156919-A1; U.S. Publ. No. US-2009-0156924-A1; U.S. Publ. No. US-2009-0163790-A1; U.S. Publ. No. US-2009-0163791-A1; U.S. Publ. No. US-2009-0178459-A1; U.S. Publ. No. US-2009-0182217-A1; U.S. Publ. No. US-2009-0192366-A1; U.S. Publ. No. US-2009-0192380-A1; U.S. Publ. No. US-2009-0192722-A1; U.S. Publ. No. US-2009-0192724-A1; U.S. Publ. No. US-2009-0192745-A1; U.S. Publ. No. US-2009-0192751-A1; U.S. Publ. No. US-2009-0203981-A1; U.S. Publ. No. US-2009-0204341-A1; U.S. Publ. No. US-2009-0216103-A1; U.S. Publ. No. US-2009-0240120-A1; U.S. Publ. No. US-2009-0240128-A1; U.S. Publ. No. US-2009-0240193-A1; U.S. Publ. No. US-2009-0242399-A1; U.S. Publ. No. US-2009-0242425-A1; U.S. Publ. No. US-2009-0247855-A1; U.S. Publ. No. US-2009-0247856-A1; U.S. Publ. No. US-2009-0287073-A1; U.S. Publ. No. US-2009-0287074-A1; U.S. Publ. No. US-2009-0299155-A1; U.S. Publ. No. US-2009-0299156-A1; U.S. Publ. No. US-2009-0299162-A1; U.S. Publ. No. US-2009-0299276-A1; U.S. Publ. No. US-2010-0010324-A1; U.S. Publ. No. US-2010-0010331-A1; U.S. Publ. No. US-2010-0010332-A1; U.S. Publ. No. US-2010-0016687-A1; U.S. Publ. No. US-2010-0016698-A1; U.S. Publ. No. US-2010-0022855-A1; U.S. Publ. No. US-2010-0030038-A1; U.S. Publ. No. US-2010-0030053-A1; U.S. Publ. No. US-2010-0030484-A1; U.S. Publ. No. US-2010-0030485-A1; U.S. Publ. No. US-2010-0036215-A1; U.S. Publ. No. US-2010-0036216-A1; U.S. Publ. No. US-2010-0036222-A1; U.S. Publ. No. US-2010-0036223-A1; U.S. Publ. No. US-2010-0036224-A1; U.S. Publ. No. US-2010-0036225-A1; U.S. Publ. No. US-2010-0041971-A1; U.S. Publ. No. US-2010-0045465-A1; U.S. Publ. No. US-2010-0049024-A1; U.S. Publ. No. US-2010-0076283-A1; U.S. Publ. No.

US-2010-0081908-A1; U.S. Publ. No. US-2010-0081910-A1; U.S. Publ. No. US-2010-0087724-A1; U.S. Publ. No. US-2010-0096259-A1; U.S. Publ. No. US-2010-0119693-A1; U.S. Publ. No. US-2010-0121169-A1; U.S. Publ. No. US-2010-0145172-A1; U.S. Publ. No. US-2010-0160760-A1; U.S. Publ. No. US-2010-0161269-A1; U.S. Publ. No. US-2010-0168540-A1; U.S. Publ. No. US-2010-0168541-A1; U.S. Publ. No. US-2010-0168542-A1; U.S. Publ. No. US-2010-0168543-A1; U.S. Publ. No. US-2010-0168544-A1; U.S. Publ. No. US-2010-0168545-A1; U.S. Publ. No. US-2010-0168546-A1; U.S. Publ. No. US-2010-0168657-A1; U.S. Publ. No. US-2010-0174157-A1; U.S. Publ. No. US-2010-0174158-A1; U.S. Publ. No. US-2010-0174163-A1; U.S. Publ. No. US-2010-0174164-A1; U.S. Publ. No. US-2010-0174165-A1; U.S. Publ. No. US-2010-0174166-A1; U.S. Publ. No. US-2010-0174167-A1; U.S. Publ. No. US-2010-0174168-A1; U.S. Publ. No. US-2010-0179400-A1; U.S. Publ. No. US-2010-0179401-A1; U.S. Publ. No. US-2010-0179402-A1; U.S. Publ. No. US-2010-0179404-A1; U.S. Publ. No. US-2010-0179405-A1; U.S. Publ. No. US-2010-0179407-A1; U.S. Publ. No. US-2010-0179408-A1; U.S. Publ. No. US-2010-0179409-A1; U.S. Publ. No. US-2010-0185065-A1; U.S. Publ. No. US-2010-0185069-A1; U.S. Publ. No. US-2010-0185070-A1; U.S. Publ. No. US-2010-0185071-A1; U.S. Publ. No. US-2010-0185072-A1; U.S. Publ. No. US-2010-0185075-A1; U.S. Publ. No. US-2010-0191082-A1; U.S. Publ. No. US-2010-0198035-A1; U.S. Publ. No. US-2010-0198036-A1; U.S. Publ. No. US-2010-0212583-A1; U.S. Publ. No. US-2010-0214104-A1; U.S. Publ. No. US-2010-0021755-A1; U.S. Publ. No. US-2010-0217557-A1; U.S. Publ. No. US-2010-0223013-A1; U.S. Publ. No. US-2010-0223022-A1; U.S. Publ. No. US-2010-0223023-A1; U.S. Publ. No. US-2010-0228109-A1; U.S. Publ. No. US-2010-0228497-A1; U.S. Publ. No. US-2010-0234707-A1; U.S. Publ. No. US-2010-0234796-A1; U.S. Publ. No. US-2010-0235106-A1; U.S. Publ. No. US-2010-0240975-A1; U.S. Publ. No. US-2010-0240976-A+B2601; U.S. Publ. No. US-2010-0256779-A1; U.S. Publ. No. US-2010-0261987-A1; U.S. Publ. No. US-2010-0274107-A1; U.S. Publ. No. US-2010-0280341-A1; U.S. Publ. No. US-2010-0286496-A1; U.S. Publ. No. US-2010-0298684-A1; U.S. Publ. No. US-2010-0305869-A1; U.S. Publ. No. US-2010-0324403-A1; U.S. Publ. No. US-2010-0331648-A1; U.S. Publ. No. US-2010-0331655-A1; U.S. Publ. No. US-2010-0331656-A1; U.S. Publ. No. US-2010-0331657-A1; U.S. Publ. No. US-2011-0004085-A1; U.S. Publ. No. US-2011-0009727-A1; U.S. Publ. No. US-2011-0024043-A1; U.S. Publ. No. US-2011-0024307-A1; U.S. Publ. No. US-2011-0027127-A1; U.S. Publ. No. US-2011-0027453-A1; U.S. Publ. No. US-2011-0027458-A1; U.S. Publ. No. US-2011-0028815-A1; U.S. Publ. No. US-2011-0028816-A1; U.S. Publ. No. US-2011-0046467-A1; U.S. Publ. No. US-2011-0077490-A1; U.S. Publ. No. US-2011-0118579-A1; U.S. Publ. No. US-2011-0118580-A1; U.S. Publ. No. US-2011-0124992-A1; U.S. Publ. No. US-2011-0124997-A1; U.S. Publ. No. US-2011-0125410-A1; U.S. Publ. No. US-2011-0130970-A1; U.S. Publ. No. US-2011-0130971-A1; U.S. Publ. No. US-2011-0130998-A1; U.S. Publ. No. US-2011-0137601-A1; U.S. Publ. No. US-2011-0144465-A1; U.S. Publ. No. US-2005-0056552-A1; and U.S. Publ. No. US-2005-0182451-A1.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for configuring alert settings of a glucose monitoring system, comprising:
   providing a receiver module having a set of configurable alert settings, wherein each of the set of configurable alert settings is initially set to a first, default setting configuration;
   coupling the receiver module to a secondary display device having a user interface capable of receiving user input;
   receiving user input from the secondary display device indicative of one or more alert setting modifications;
   modifying one or more of the set of alert settings in accordance with the user input into a second configuration that is different than the first, default setting configuration and
   automatically resetting the set of configurable alert settings to the first, default setting configuration upon a detection of a predetermined event, wherein the predetermined event comprises a data corruption error or a device hacking indication.

2. The method of claim 1, wherein the set of configurable alert settings comprises one or more settings selected from a group consisting of: a hypoglycemic setting, a hyperglycemic setting, a rate-of-change setting and a calibration setting.

3. The method of claim 1, wherein the first, default setting configuration comprises a setting indicative of a hypoglycemic event threshold and a setting indicative of a hyperglycemic event threshold, the method further comprising activating an alarm of the receiving module if one of the event thresholds is exceeded.

4. A continuous glucose monitoring system for monitoring a glucose concentration of a host, the system comprising:
   a continuous glucose sensor;
   a sensor electronics unit electrically coupled to the continuous glucose sensor, the sensor electronics unit configured to generate sensor data indicative of a glucose concentration of a host using the continuous glucose sensor and configured to intermittently wirelessly transmit the sensor data; and
   a mobile digital device having a glucose monitoring application stored in non-transitory memory therein, the glucose monitoring application comprising instructions that, when executed by a processor of the mobile digital device, causes the mobile digital device to
receive and process the sensor data transmitted from the sensor electronics unit,
display a user-selectable icon associated with the glucose monitoring application on a user interface of the mobile digital device, wherein the icon includes a displayed glucose value generated from the processed sensor data and
launch the glucose monitoring application in response to detection of a user selection of the user-selectable icon,
wherein the instructions of the glucose monitoring application, when executed by the processor, causes the mobile digital device to update the displayed glucose concentration on the user-selectable icon based on the received and processed sensor data including a new glucose concentration of the host detected by the continuous glucose sensor.

5. The system of claim 4, wherein the mobile digital device is a smart phone.

6. The system of claim 4, wherein the mobile digital device is configured to run the continuous glucose monitoring application in a background mode and a foreground mode, wherein the launch of the glucose monitoring application causes the mobile digital device to run the continuous glucose monitoring application in the foreground mode.

7. The system of claim 6, wherein the mobile digital device performs the displaying of the user-selectable icon in the background mode.

8. The system of claim 7, wherein the glucose monitoring application comprises one or more user-modifiable alert settings that cause the mobile digital device to trigger an alarm if the received sensor data satisfy the one or more alert settings.

9. The system of claim 8, wherein the mobile digital device is configured to trigger the alarm while in the background mode.

10. The system of claim 6, wherein the mobile digital device displays a retrospective view of the received sensor data while the glucose monitoring application is in the foreground mode.

11. The system of claim 4, wherein the continuous glucose monitoring application was downloaded on the mobile digital device from a remote server.

* * * * *